United States Patent
McLeod et al.

(10) Patent No.: US 12,226,072 B2
(45) Date of Patent: Feb. 18, 2025

(54) SYSTEMS AND METHODS FOR IDENTIFYING DIFFERENTIATED BLOOD VESSELS AND REGISTERING IMAGING DATA FROM DIFFERENT IMAGING MODALITIES BASED ON SUBSURFACE IMAGE SCANNING

(71) Applicant: Intuitive Surgical Operations, Inc., Sunnyvale, CA (US)

(72) Inventors: A. Jonathan McLeod, Sunnyvale, CA (US); Mahdi Azizian, San Jose, CA (US); Daniel Proksch, San Jose, CA (US); Pourya Shirazian, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 423 days.

(21) Appl. No.: 17/638,322

(22) PCT Filed: Aug. 26, 2020

(86) PCT No.: PCT/US2020/047999
§ 371 (c)(1),
(2) Date: Feb. 25, 2022

(87) PCT Pub. No.: WO2021/041545
PCT Pub. Date: Mar. 4, 2021

(65) Prior Publication Data
US 2022/0296303 A1   Sep. 22, 2022

Related U.S. Application Data

(60) Provisional application No. 62/893,040, filed on Aug. 28, 2019.

(51) Int. Cl.
*A61B 34/10* (2016.01)
*A61B 1/00* (2006.01)
(Continued)

(52) U.S. Cl.
CPC ........ *A61B 1/000094* (2022.02); *A61B 34/10* (2016.02); *A61B 34/20* (2016.02);
(Continued)

(58) Field of Classification Search
None
See application file for complete search history.

(56) References Cited

U.S. PATENT DOCUMENTS

2013/0129175 A1 * 5/2013 Razzaque .............. A61B 34/20
  382/131
2014/0303491 A1 10/2014 Shekhar et al.
(Continued)

FOREIGN PATENT DOCUMENTS

EP        2942029 A1    11/2015
WO   WO-2017060865 A2    4/2017

OTHER PUBLICATIONS

International Search Report and Written Opinion for Application No. PCT/US2020/047999, mailed Jan. 28, 2021, 13 pages.
(Continued)

*Primary Examiner* — Haris Sabah

(57) ABSTRACT

An exemplary image registration system identifies a subsurface structure at a surgical site based on subsurface imaging data from a subsurface image scan at the surgical site. The image registration system uses the identified subsurface structure at the surgical site for a registration of endoscopic imaging data from an endoscopic imaging modality with additional imaging data from an additional imaging modality. Corresponding systems and methods are also disclosed.

20 Claims, 13 Drawing Sheets

(51) Int. Cl.
    *A61B 34/20*    (2016.01)
    *G06T 7/00*     (2017.01)
    *A61B 6/02*     (2006.01)
(52) U.S. Cl.
    CPC ............ *G06T 7/0012* (2013.01); *A61B 6/022* (2013.01); *A61B 2034/107* (2016.02); *A61B 2034/2055* (2016.02); *G06T 2207/10068* (2013.01); *G06T 2207/30101* (2013.01)

(56) References Cited

U.S. PATENT DOCUMENTS

| | | | | |
|---|---|---|---|---|
| 2015/0190035 | A1* | 7/2015 | Adler | A61B 1/0605 600/109 |
| 2017/0265943 | A1* | 9/2017 | Sela | A61B 34/20 |
| 2020/0054399 | A1* | 2/2020 | Duindam | A61B 34/37 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2020/047999, mailed Mar. 10, 2022, 10 pages.

* cited by examiner

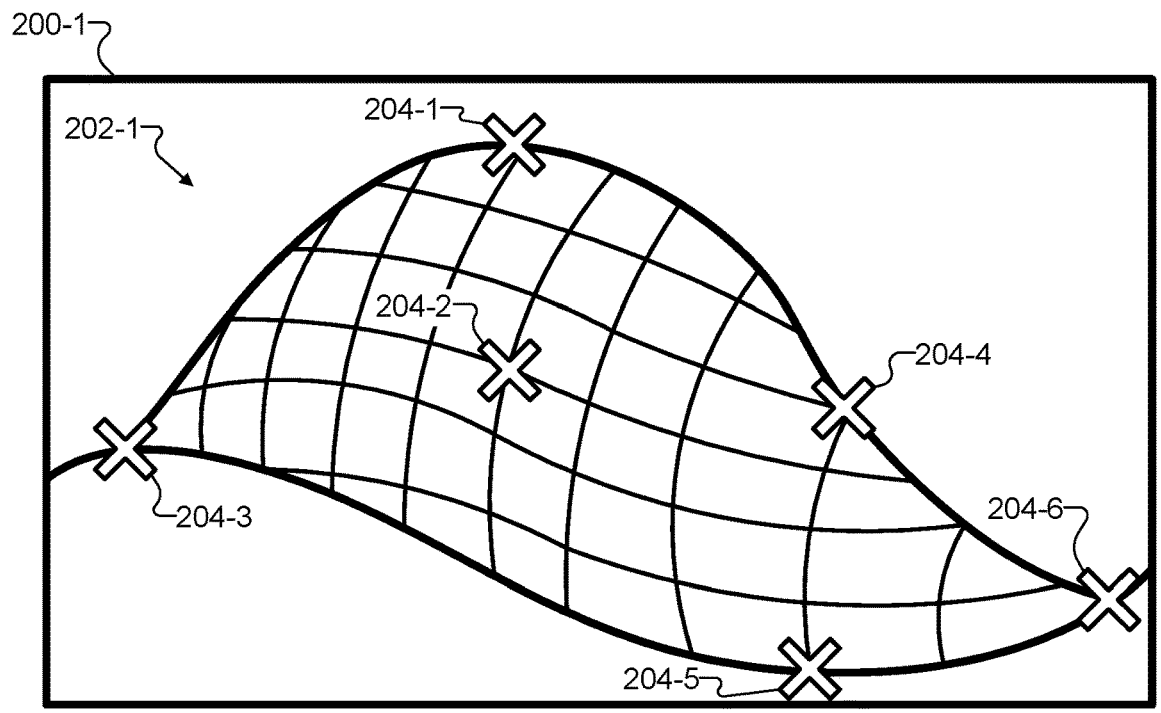
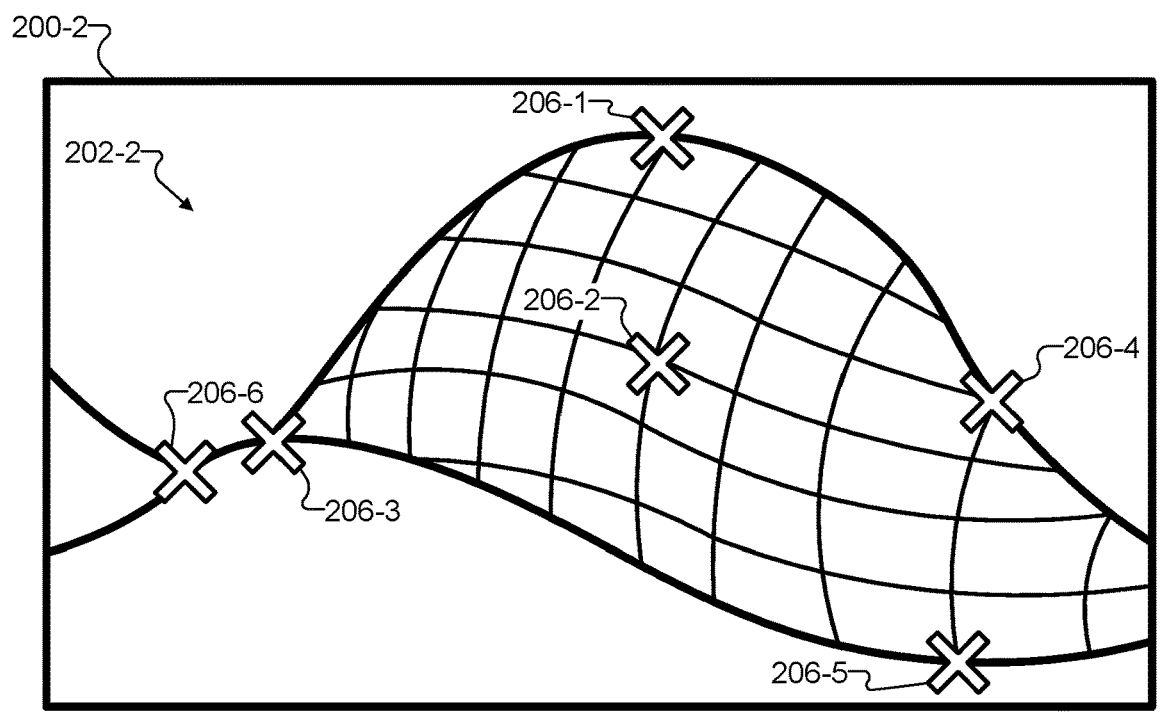
Fig. 2

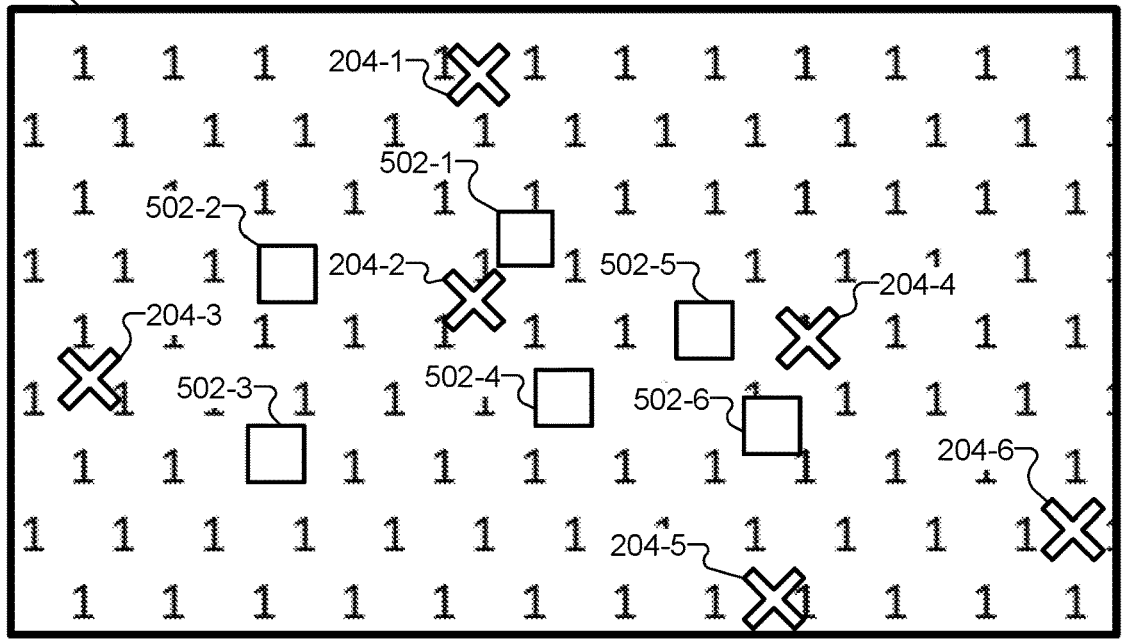
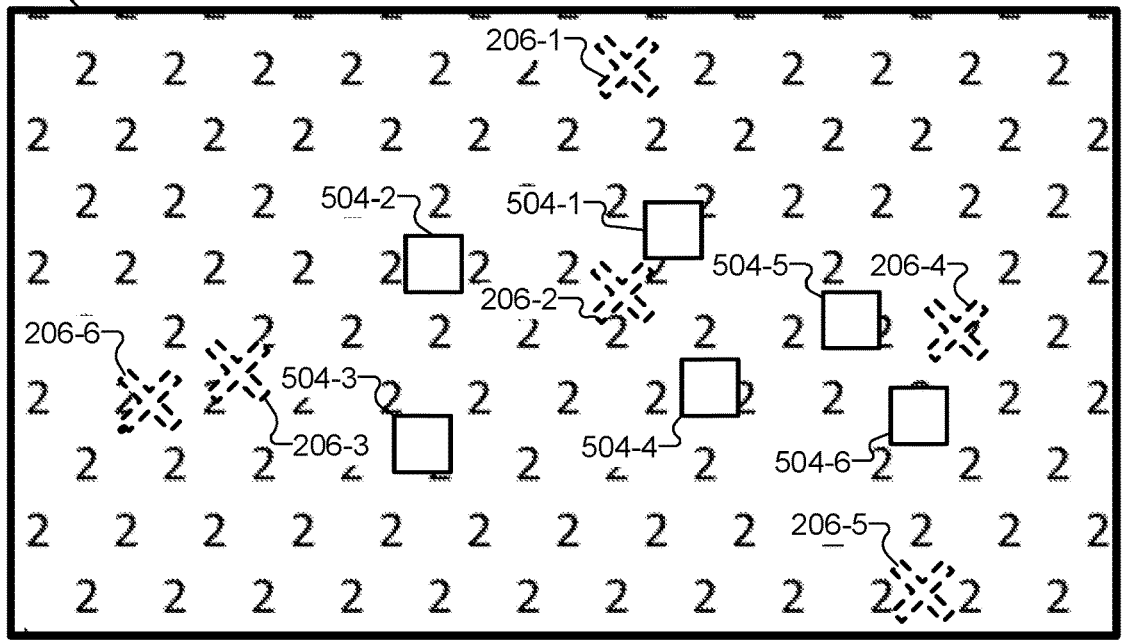
Fig. 5

SYSTEMS AND METHODS FOR IDENTIFYING DIFFERENTIATED BLOOD VESSELS AND REGISTERING IMAGING DATA FROM DIFFERENT IMAGING MODALITIES BASED ON SUBSURFACE IMAGE SCANNING

RELATED APPLICATIONS

The present application is a U.S. National Stage Application under 35 U.S.C. § 371 of International Application No. PCT/US2020/047999, filed on Aug. 26, 2020, which claims priority to U.S. Provisional Patent Application No. 62/893,040, filed on Aug. 28, 2019, the contents of which are hereby incorporated by reference in their entirety.

BACKGROUND INFORMATION

During a surgical procedure, an endoscope may be used to capture endoscopic imagery of a surgical site. The endoscopic imagery may be presented to a surgeon by way of a display device so that the surgeon may visualize the surgical site while performing the surgical procedure.

In some scenarios, one or more additional imaging modalities (other than the endoscopic imaging modality) may be used to capture additional imagery of the surgical site that may also be presented to the surgeon. Such additional imagery may be captured preoperatively or intraoperatively, and may be captured, for instance, by way of an ultrasound scan, a computerized tomography ("CT") scan, a magnetic resonance imaging ("MRI") scan, a fluoroscopic imaging scan, and/or another suitable imaging modality configured to capture imagery of the surgical site.

Imagery captured by different imaging modalities may be presented to facilitate the surgeon in visualizing the surgical site, but the surgeon may still find it to be difficult and/or inconvenient to conceptualize the surgical site and synthesize a mental model of the surgical site based on different types of imagery. This is particularly true when the imagery represents different content captured in different ways (e.g., surface anatomy content versus subsurface anatomy content, preoperatively-captured content versus intraoperatively-captured content, etc.). As such, there remains room to improve the processing and presenting of imagery captured by different imaging modalities.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions to identify a subsurface structure at a surgical site based on subsurface imaging data from a subsurface image scan at the surgical site; and use the identified subsurface structure at the surgical site for a registration of endoscopic imaging data from an endoscopic imaging modality with additional imaging data from an additional imaging modality.

Another exemplary system also includes a memory storing instructions and a processor communicatively coupled to the memory and configured to execute the instructions to perform various operations intraoperatively during a surgical operation at a surgical site. For example, the various operations performed by the processor may include operations to access intraoperative endoscopic imaging data from an endoscope; access intraoperative subsurface imaging data from a subsurface imaging module; access alignment parameters representative of the registration of the intraoperative endoscopic imaging data with the intraoperative subsurface imaging data; access preoperative scan data captured by way of an additional imaging modality distinct from an endoscopic imaging modality, the preoperative scan data representative of a three-dimensional ("3D") model of anatomy at the surgical site; identify a subsurface structure at the surgical site based on the intraoperative subsurface imaging data and the alignment parameters; and/or use the identified subsurface structure at the surgical site for a registration of the intraoperative endoscopic imaging data with the preoperative scan data representative of the 3D model of the anatomy at the surgical site.

An exemplary method includes an image registration system identifying a subsurface structure at a surgical site based on subsurface imaging data from a subsurface image scan at the surgical site, and using the identified subsurface structure at the surgical site for a registration of endoscopic imaging data from an endoscopic imaging modality with additional imaging data from an additional imaging modality.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 2 illustrates exemplary aspects of a registration of a first set of imaging data with a second set of imaging data according to principles described herein.

FIG. 5 illustrates exemplary aspects of a registration of endoscopic imaging data from an endoscopic imaging modality with additional imaging data from an additional imaging modality according to principles described herein.

DETAILED DESCRIPTION

Figure 1:
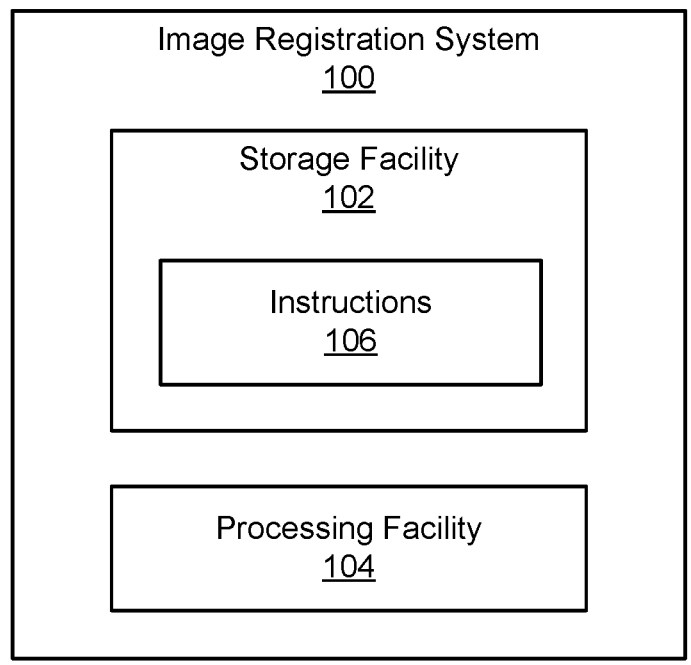
FIG. 1 illustrates an exemplary image registration system for registering imaging data from different imaging modalities based on subsurface image scanning according to principles described herein.

Systems and methods for registering imaging data from different imaging modalities based on subsurface image scanning are described herein. Various types of surgical procedures may be planned or performed at a surgical site that may include anatomy of a body upon which the surgical procedure is performed (or is to be performed), anatomy proximate to the anatomy being (or that is to be) operated on, and other areas (e.g., open space) proximate to this anatomy. The anatomy being operated on and the surrounding anatomy may include various subsurface structures that are located beneath or behind surface anatomy being operated on during the procedure. For example, subsurface structures may include such structures as vasculature comprised of a plurality of blood vessels (e.g., arteries, veins, etc.), bone structures, tissue masses (e.g., cancerous and/or non-cancerous tumors, cell growths, etc.), organs, tendons, muscles, ligaments, cartilage, nerves, fat, and/or other subsurface anatomy that may be identified, by certain imaging modalities, to be beneath or behind the surface being operated on.

Systems and methods described herein may use subsurface imaging data from a subsurface image scan at a surgical site to identify locations of subsurface structures at the surgical site, and then use the identified locations of the subsurface structures for a registration of data from different imaging modalities (e.g., to register or to refine a registration of the data from the different imaging modalities). As will be described in more detail below, any type of imaging scan configured to determine subsurface image data may be used as the subsurface image scan in the examples described herein. For instance, the subsurface image scan may be a suitable ultrasound scan (e.g., a standard ultrasound scan, a contrast-enhanced ultrasound scan, a harmonic imaging scan with or without contrast, a scan employing ultrasound elastography, a tomographic ultrasound, etc.) that is configured to detect subsurface structures such as vasculature, bone structures, or tissue masses that are not visible using a visual light modality such as an endoscope. As another example, a vascular ultrasound scan such as a doppler ultrasound scan or a standard ultrasound scan employing a vessel segmentation algorithm may be employed to identify vasculature specifically. In still other examples, the subsurface image scan may be implemented by a non-ultrasound imaging modality such as optical coherence tomography, fluorescence imaging, hyperspectral imaging, or another suitable type of image that is capable of mapping various subsurface structures (e.g., vasculature, bone structures, tissue masses, etc.) of a body.

Various details and exemplary embodiments for the types of imaging modalities that may be registered to one another, the circumstances under which the imaging modalities may be employed, and so forth will be described in more detail below. Additionally, as will further be described herein, the registration of imaging data from different imaging modalities may be used to provide a composite image of the surgical site (e.g., a composite image that shows preoperative and intraoperative imaging data integrated together into a single image view) for display by a display device to facilitate the surgical procedure.

One exemplary image registration system may include a memory storing instructions and a processor communicatively coupled to the memory and configured to execute the instructions to perform certain operations. For instance, the processor may identify a subsurface structure at a surgical site based on subsurface imaging data from a subsurface image scan at the surgical site. The processor of the image registration system may also use the identified subsurface structure at the surgical site for a registration of endoscopic imaging data from an endoscopic imaging modality with additional imaging data from an additional imaging modality. For instance, the subsurface structure may be used to initially generate or to correct (e.g., refine, revise, update, etc.) the registration of the endoscopic imaging data with the additional imaging data.

Another exemplary image registration system may include an endoscope, a subsurface imaging module, and a processor. These components may operate together during a surgical operation at a surgical site (i.e., "intraoperatively") to provide to a user (e.g., to a surgeon or surgical team member) a combination of imagery captured intraoperatively and captured prior to the surgical operation (i.e., "preoperatively"). For instance, the endoscope may be configured to capture intraoperative endoscopic imaging data, the subsurface imaging module may be configured to capture intraoperative subsurface imaging data, and the processor may be configured to access, along with accessing the intraoperative endoscopic imaging data from the endoscope and the intraoperative subsurface imaging data from the subsurface imaging module, preoperative scan data captured by way of an additional imaging modality. The additional imaging modality may be distinct from an endoscopic imaging modality used by the endoscope, and may include, for example, a preoperative magnetic resonance imaging ("MRI") scan, a preoperative computerized tomography ("CT") scan, a preoperative ultrasound scan, or the like. In some examples, the preoperative scan data may be representative of a three-dimensional ("3D") model of anatomy at the surgical site.

Along with accessing the endoscopic imaging data, the subsurface imaging data, and the preoperative scan data, the processor may be further configured to access alignment parameters representative of a registration of the intraoperative endoscopic imaging data with the intraoperative subsurface imaging data. Accordingly, the processor may identify a subsurface structure at the surgical site in relation to the intraoperative endoscopic imaging data based on the intraoperative subsurface imaging data and the alignment parameters, and may use the identified subsurface structure at the surgical site for a registration of the intraoperative endoscopic imaging data with the preoperative scan data (e.g., representative of the 3D model of the anatomy at the surgical site).

Systems and methods described herein may provide various advantages and benefits. For example, systems and methods described herein may facilitate initially registering or correcting a registration of different sets of imaging data captured by way of different imaging modalities to align imaging data that would be difficult, impractical, or not possible to align and register accurately in other ways. For instance, it may not be possible to align and register endoscopic imaging data that depicts surface anatomy with additional imaging data that represents subsurface anatomy (e.g., MRI imaging data, CT imaging data, ultrasound imaging data, a 3D anatomical model generated based on any of these types of data, etc.) using a conventional technique of identifying and matching up common visual features depicted or represented in both imaging datasets. This is because the endoscopic imaging data may depict completely different features (e.g., surface anatomy features) than the features represented in the additional imaging data (e.g., subsurface anatomy features).

Systems and methods described herein thus may take advantage of the facts that 1) subsurface imaging data from a subsurface image scan at the surgical site can be accurately registered to endoscopic data in other ways (e.g., based on kinematic and/or visual data indicating where a subsurface imaging module is with respect to an endoscope); and 2) the subsurface imaging data indicates the location of subsurface structures at the surgical site that are also represented in the additional imaging data. Accordingly, subsurface structures identified based on the subsurface image data may be used to register the endoscopic imaging data with the additional imaging data even if these datasets are captured at different times (e.g., preoperatively and intraoperatively), include deformed anatomical representations (e.g., due to gravity or pressing of instruments that are applied in different ways when the different imaging data is captured), and so forth.

Moreover, the accurate and efficient registration of different types of imaging data provided by systems and methods described herein may allow for direct benefits to users of a computer-assisted surgical system. For example, systems and methods described herein may allow imagery captured by different imaging modalities to be integrated into composite imagery of a surgical site in a manner that produces, within the composite imagery, an integrated and intuitive depiction of imagery of the surgical site as captured by the different imaging modalities. Systems and methods described herein may present the generated composite imagery to a user of a computer-assisted surgical system, such as a surgeon utilizing the computer-assisted surgical system to perform a surgical procedure. The presented composite imagery may be visually intuitive to the surgeon; may reduce the complexity of the surgical procedure for the surgeon (e.g., by eliminating the need for the surgeon to mentally align imagery of the surgical site that is presented separately in a non-integrated manner); and/or may allow the surgeon to concurrently, conveniently, and intuitively visualize surface and subsurface anatomy integrated in composite imagery. Moreover, the presented composite imagery may be user-customizable to allow the surgeon to provide input to conveniently and dynamically select a portion of a surgical site that is to be augmented such that the selected portion may be viewed using a different imaging modality than is used to view another portion of the surgical site. For example, the systems and methods may enable a surgeon to select a portion of the surgical site at which imagery of subsurface anatomy is displayed as an augmentation to imagery of surface anatomy being displayed.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary image registration system 100 ("system 100") for registering imaging data from different imaging modalities based on subsurface image scanning. System 100 may be included in, implemented by, or connected to one or more components of a computer-assisted surgical system such as an exemplary computer-assisted surgical system that will be described below in relation to FIG. 10. For example, system 100 may be implemented by one or more components of a computer-assisted surgical system such as a manipulating system, a user control system, or an auxiliary system. As another example, system 100 may be implemented by a stand-alone computing system communicatively coupled to a computer-assisted surgical system.

As shown in FIG. 1, system 100 may include, without limitation, a storage facility 102 and a processing facility 104 selectively and communicatively coupled to one another. Facilities 102 and 104 may each include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into fewer facilities, such as into a single facility, or divided into more facilities as may serve a particular implementation. In some examples, each of facilities 102 and 104 may be distributed between multiple devices and/or multiple locations as may serve a particular implementation.

Storage facility 102 may maintain (e.g., store) executable data used by processing facility 104 to perform any of the functionality described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with registering imaging data from different imaging modalities based on subsurface image scanning. For example, processing facility 104 may be configured to identify a subsurface structure at a surgical site based on subsurface imaging data from a subsurface imaging scan at the surgical site (e.g., a doppler ultrasound scan, a standard ultrasound scan employing a vessel segmentation algorithm, a contrast-enhanced ultrasound scan, a harmonic imaging scan, a scan employing ultrasound elastography, a tomographic ultrasound, another type of ultrasound scanning allowing for two-dimensional ("2D"), 3D, or other types of subsurface structure maps to be generated, etc.) or based on data derived by way of another suitable type of subsurface image scanning (e.g., optical coherence tomography, fluorescence imaging, hyperspectral imaging, etc.). Processing facility 104 may use the identified subsurface structure at the surgical site for a registration of endoscopic imaging data from an endoscopic imaging modality with additional imaging data from an additional (e.g., non-endoscopic) imaging modality.

Certain implementations of system 100 may be specifically configured to register imaging data from different imaging modalities based on subsurface image scanning in real time or near real time, such as by performing the above or other operations intraoperatively during a surgical operation at the surgical site. For instance, an exemplary implementation of system 100 may include a memory storing instructions and a processor communicatively coupled to the memory and configured to execute the instructions to perform various functions intraoperatively during the surgical operation at the surgical site. For example, processing facility 104 may be configured, in the following sequence or another suitable sequence, to 1) access intraoperative endoscopic imaging data from an endoscope; 2) access intraoperative subsurface imaging data from a subsurface imaging module; 3) access alignment parameters representative of a registration of the intraoperative endoscopic imaging data with the intraoperative subsurface imaging data; 4) access preoperative scan data captured by way of an additional imaging modality distinct from an endoscopic imaging modality (e.g., where the preoperative scan data may be representative of a 3D model of anatomy at the surgical site); 5) identify a subsurface structure at the surgical site based on the intraoperative subsurface imaging data and the alignment parameters; and 6) use the identified subsurface structure at the surgical site for a registration of the intraoperative endoscopic imaging data with the preoperative scan data representative of the 3D model of the anatomy at the surgical site.

These and other functions that may be performed by processing facility 104 are described herein. In the description that follows, any references to functions performed by system 100 may be understood to be performed by processing facility 104 based on instructions 106 stored in storage facility 102.

FIG. 2 illustrates exemplary aspects of a registration of a first set of imaging data 200-1 with a second set of imaging data 200-2. The registration of first imaging data with second imaging data may refer, in certain examples, to a mapping of image datapoints from the first imaging data to corresponding image datapoints in the second imaging data, such that the registration allows for the image datasets to be aligned from a particular viewpoint. For example, as illustrated in FIG. 2, imaging data 200-1 is representative of a depiction 202-1 of an anatomical structure at a surgical site (e.g., an internal organ or portion thereof, etc.), and imaging data 200-2 is representative of a depiction 202-2 of the same anatomical structure (albeit captured from a slightly different viewpoint such that imaging data 200-1 and 200-2 are similar but not identical). The registration of imaging data 200-1 with imaging data 200-2 may thus involve determining whether various features 204 (e.g., features 204-1 through 204-6) in depiction 202-1 correspond to like features 206 (e.g., features 206-1 through 206-6) in depiction 202-2.

As shown, for example, features 204-1 and 206-1 may be determined to be a match (i.e., representative of the same physical features), as may the feature pairs 204-2 and 206-2, 204-3 and 206-3, 204-4 and 206-4, and 204-5 and 206-5. In this example, a feature of each depiction is also called out that does not correspond to a like feature in the other depiction. Specifically, no datapoint in depiction 202-2 of imaging data 200-2 may correspond to the datapoint representing feature 204-6 in depiction 202-1 of imaging data 200-1, nor may any datapoint in depiction 202-1 correspond to the datapoint representing feature 206-6 in depiction 202-2. Imaging data 200-1 may be registered with imaging data 200-2 by identifying a sufficient number of corresponding datapoint pairs (e.g., datapoint pairs representative of like features 204 and 206) that depiction 202-1 can be aligned with depiction 202-2 with respect to a particular viewpoint (e.g., either the viewpoint from which imaging data 200-1 was captured, the viewpoint from which imaging data 200-2 was captured, or another suitable viewpoint).

In the example of FIG. 2, it will be understood that depictions 202-1 and 202-2 may look so similar because the respective images of each imaging data 200-1 and 200-2 are captured by way of the same imaging modality (e.g., in the same manner, by the same capture device, using the same imaging technology, etc.). Additionally, and because of the visual similarities, registering imaging data 200-1 with imaging data 200-2 may be performed in a relatively straightforward way by identifying features 204 in depiction 202-1, identifying features 206 in depiction 202-2, and matching features from each group to identify corresponding datapoints.

However, while the example of FIG. 2 illustrates aspects of registering imaging data captured by a single imaging modality, it will also be understood that, in certain examples, it may be desirable to register imaging data from one imaging modality (e.g., an endoscopic imaging modality) with imaging data from a different imaging modality (e.g., an additional imaging modality such as a CT scan, an MRI scan, or the like). In these latter cases, additional challenges and/or complexities may accompany the registration.

As one example, different imaging modalities may capture depictions or other representations of anatomy at different points in time. For instance, an endoscopic imaging modality may comprise an intraoperative scan of anatomy at a surgical site, and, as such, may be performed in real-time as an operation is ongoing. Similarly, an ultrasound scan or a fluoroscopic imaging scan (in which a fluorescent die is injected into the body to facilitate imaging at specific frequencies at which the die exhibits fluorescent properties) may similarly be employed intraoperatively, either in real time as the operation is being performed or during the operation period while active surgical operations are temporarily put on hold while the imaging is performed. Conversely, other types of imaging modalities may capture depictions or other representations of anatomy at some point in time prior to an operation being performed at the surgical site (e.g., immediately prior, a day or more prior, etc.). For example, an imaging modality comprising a CT scan, an MRI scan, an ultrasound scan, an x-ray scan, a 3D modeling generation based on data from any such scans, or another other suitable imaging modality may be performed at a different time when the body is in a different state. For example, a patient upon which the surgical operation is performed may be positioned differently (e.g., laying on the back versus laying on the side), or may have other significant differences (e.g., fasting or not fasting) during a preoperative time when one imaging modality is used and during an intraoperative time when another imaging modality is used. In other examples, different modalities may be used at the same time (e.g., both preoperatively, both intraoperatively, etc.) or at times that are different in other ways than this example (e.g., different preoperative times, different intraoperative times, a preoperative and a postoperative time, an intraoperative and a postoperative time, etc.).

As another exemplary complexity that may accompany registration when different modalities are used, like features such as features 204 and 206 may not be present in respective depictions or other representations (e.g., 3D models, etc.) of imaging data being registered. This may occur because different imaging modalities may capture and represent anatomy in different ways. For instance, one imaging modality such as an endoscopic imaging modality may capture data representative of a depiction of surface anatomy (i.e., anatomy that can be readily imaged by reflecting visible light off of the anatomy), while additional imaging modalities such as an ultrasound scan of the surgical site, a CT scan of the surgical site, an MRI scan of the surgical site, or an x-ray scan of the surgical site may capture data representative of subsurface anatomy (i.e., anatomy behind or beneath the surface anatomy that can only be imaged by using advanced techniques involving sound waves, light waves outside of the visible spectrum, or the like).

Because different visible features may be present on surface anatomy and on subsurface anatomy, the feature-matching registration illustrated and described with respect to FIG. 2 may be insufficient to register endoscopic imaging data depicting surface anatomy with additional imaging data representative of subsurface anatomy.

To overcome these challenges, systems and methods described herein may rely on certain subsurface structures such as vasculature, bone structures, tissue masses, or other such subsurface anatomy that is identifiable with respect to various imaging modalities even when used at different times and/or representing different layers (e.g., surface or subsurface layers) of anatomy. For example, the position of vasculature, as identified by vascular imaging data from a vascular image scan that is registered with endoscopic imagery by way of kinematic, visual, or other suitable techniques, may be used to register the endoscopic depiction of surface anatomy with a 3D representation of subsurface anatomy included in additional imaging data captured by way of a non-endoscopic imaging modality such as a CT or MRI scan. Similarly, as another example, the position of certain bone structures, tissue masses, and/or other subsurface structures may be identified by subsurface imaging data from subsurface image scans that are likewise registered with endoscopic imagery by way of kinematic, visual, and/or other suitable techniques. As with the vasculature structures mentioned above, these subsurface structures too may be used to register the endoscopic depiction of surface anatomy with a 3D representation of subsurface anatomy included in additional imaging data captured by way of a non-endoscopic imaging modality such as a CT or MRI scan. Accordingly, system 100 may use identified subsurface structures such as vasculature, bone structures, tissue masses, or other suitable structures as an implementation of or substitute for features 204 and 206 as system 100 either generates or corrects (e.g., refines, updates, revises, etc.) a set of alignment parameters representative of the registration. For example, the set of alignment parameters may be associated with transformation matrices, translation matrices, and the like.

Alignment parameters included in a set of alignment parameters generated or corrected by system 100 may be configured to define a spatial transformation between endoscopic imaging data and additional imaging data. In various examples, the spatial transformation defined by the set of alignment parameters may relate to a rigid transformation (e.g., including translation and rotation operations) from one set of imaging data to another set of imaging data, an affine transformation (e.g., including general linear transformations, scaling, and skew operations) from one set of imaging data to the other, a deformable registration (e.g., including nonlinear transformations with different parameterizations, etc.) from one set of imaging data to the other, or any other type of spatial transformation as may serve a particular implementation.

There may be various purposes for which system 100 registers one set of imaging data with another set of imaging data. For example, as has been mentioned, one purpose of registering first imaging data from a first imaging modality with second imaging data from a second imaging modality is to align the first and second imaging data so as to allow system 100 to generate and provide a composite image of the surgical site, for display by a display device, that includes aspects of both the first imaging data and the second imaging data as viewed from a particular viewpoint (e.g., a viewpoint of a surgeon performing a surgical procedure at the surgical site, etc.). For example, such a composite image may be based on a registration of endoscopic imaging data from an endoscopic imaging modality with additional imaging data from an additional imaging modality, and may allow for aspects of both the endoscopic and the additional imaging data to be presented to a user in a single convenient, customizable view to facilitate operations at the surgical site.

Figure 3:
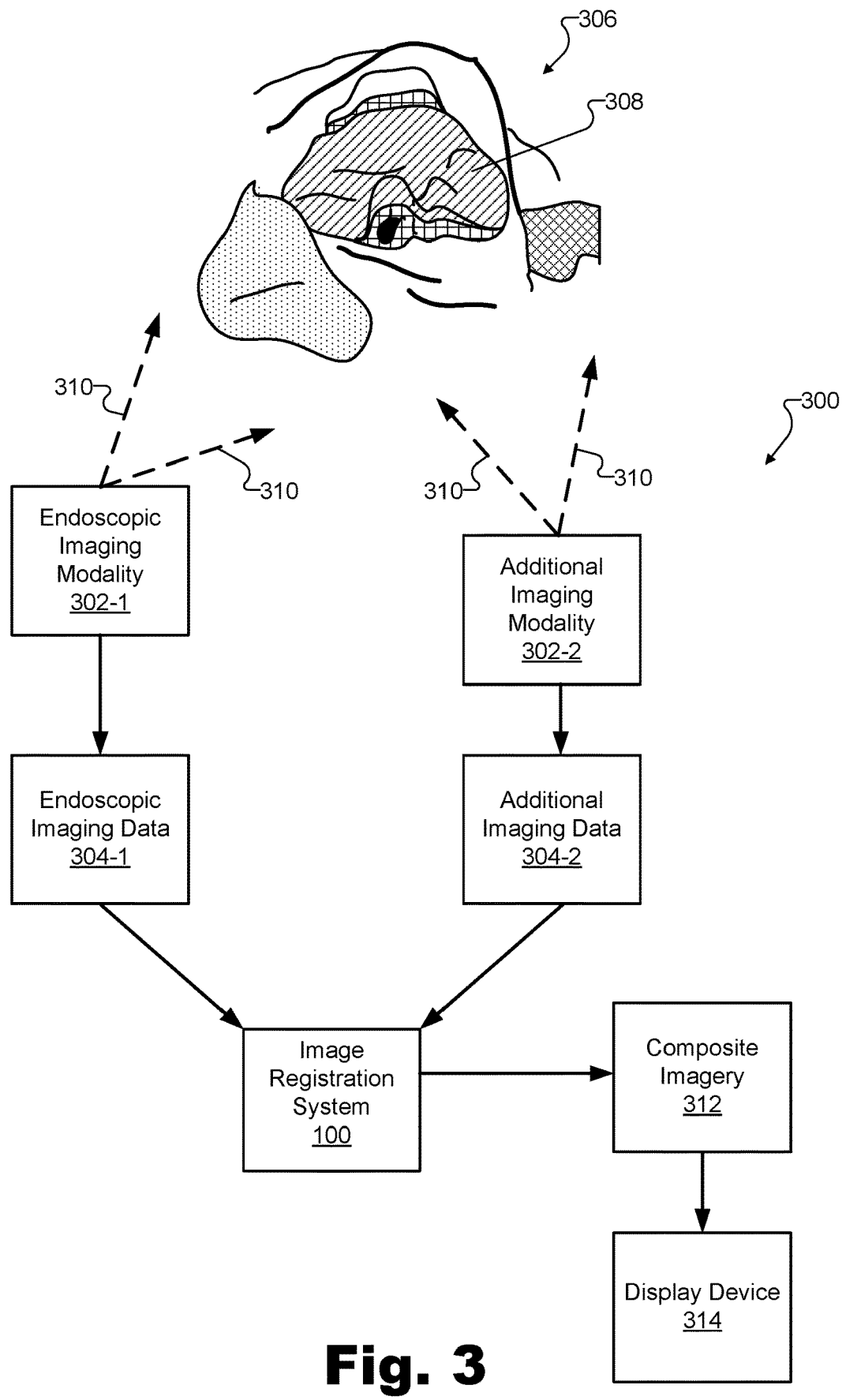
FIG. 3 illustrates an exemplary configuration in which the image registration system of FIG. 1 registers imaging data from different imaging modalities to generate composite imagery of a surgical site according to principles described herein.

To illustrate, FIG. 3 shows an exemplary configuration 300 in which system 100 registers imaging data from different imaging modalities to generate composite imagery of a surgical site. As shown, configuration 300 may include multiple imaging modalities 302 (e.g., endoscopic imaging modality 302-1 and additional imaging modality 302-2) configured to capture imaging data 304 (e.g., endoscopic imaging data 304-1 captured by way of endoscopic imaging modality 302-1 and additional imaging data 304-2 captured by way of additional imaging modality 302-2) of a surgical site 306.

Surgical site 306 may include any volumetric space associated with a surgical procedure. For example, surgical site 306 may include any part or parts of a body of a patient, such as anatomy 308 (e.g., tissue, etc.) of the patient in a space associated with the surgical procedure. Surgical site 306 may, in certain examples, be entirely disposed within the patient and may include a space within the patient near where a surgical procedure is planned to be performed, is being performed, or has been performed. For example, for a minimally invasive surgical procedure being performed on tissue internal to a patient, surgical site 306 may include the surface tissue, anatomy underlying the surface tissue, as well as space around the tissue where, for example, surgical instruments being used to perform the surgical procedure are located. In other examples, surgical site 306 may be at least partially disposed external to the patient. For instance, for an open surgical procedure being performed on a patient, part of surgical site 306 (e.g., tissue being operated on) may be internal to the patient while another part of surgical site 306 (e.g., a space around the tissue where one or more surgical instruments may be disposed) may be external to the patient. Surgical site 306 may include a real workspace in which a surgical procedure is performed, such as an actual, real-world workspace associated with a patient and in which one or more surgical instruments are used to perform the surgical procedure on the patient.

As used herein, a surgical procedure may include any medical procedure, including any diagnostic or treatment procedure in which manual and/or instrumental techniques are used on a patient to investigate or treat a physical condition of the patient. A surgical procedure may refer to any phases of a medical procedure, such as preoperative, operative (i.e., intraoperative), and postoperative phases of a surgical procedure.

Imaging modalities 302 may be configured and/or used to capture imaging data 304 representative of surgical site 306. Such a capture is represented by dashed lines 310 in FIG. 3. Imaging modalities 302 may each capture imaging data 304 of surgical site 306 in any suitable manner and imaging data 304 may take any suitable form. For instance, imaging data 304 may be implemented as data representative of a still frame image (e.g., a grayscale image, a color image, an infrared image, etc.), a video (e.g., grayscale, color, infrared video, etc.), a 3D model, or any other type of visual representation or depiction as may be useful for helping a user visualize surgical site 306 in a certain implementation. Imaging modalities 302 may also each capture imaging data 304 at any suitable time. For instance, one or more imaging modalities 302 may capture imaging data of surgical site 306 during one or more preoperative, intraoperative, and/or postoperative phases of a surgical procedure.

Endoscopic imaging modality 302-1 is a modality that involves imaging data captured by way of an endoscope (e.g., or another suitable type of endoscopic instrument) that is configured to project light (e.g., light at visible frequencies) onto anatomy at surgical site 306, and to capture photographic imagery of the anatomy as the light reflects from the anatomy to one or more image sensors associated with the endoscope. In contrast, additional imaging modality 302-2 may be a different type of imaging modality (i.e., a modality other than an endoscopic imaging modality) in certain examples. For example, as described above, additional imaging modality 302-2 may include or involve, without limitation, ultrasound imaging by an ultrasound module or machine, CT imaging by a CT machine, MRI imaging by an MRI machine, or the like. Any other suitable additional imaging modalities may be used in other examples.

In certain examples, endoscopic imaging modality 302-1 may be configured to capture imagery of surface anatomy included at surgical site 306 (e.g., an outer surface of tissue included at the surgical site), and additional imaging modality 302-2 may be configured to capture imagery of subsurface anatomy included at surgical site 306 (e.g., subsurface tissue that is behind the outer surface of tissue included at the surgical site). For example, endoscopic imaging modality 302-1 may capture images of surface tissue within a patient, and additional imaging modality 302-1 may include ultrasound, CT, or MRI imaging that captures images of subsurface tissue that, from the perspective of the endoscope, is behind and hidden from the view of the endoscope by the surface anatomy.

As mentioned above, imaging modalities 302 may each capture imaging data 304 of surgical scene 306 at any suitable time, such as during any phase(s) of a surgical procedure or operation. In certain examples, imaging modalities 302 may concurrently capture imaging data 304 of surgical site 306. For instance, endoscopic imaging modality 302-1 may capture endoscopic imagery during a surgical procedure (e.g., during an operative phase of the surgical procedure), and additional imaging modality 302-1 may concurrently capture another type of imagery during the surgical procedure. In other examples, imaging modalities 302 may capture imaging data 304 of surgical site 306 at different times and/or during different phases of the surgical procedure. For instance, endoscopic imaging modality 302-1 may capture endoscopic imagery during an operative phase of the surgical procedure, and additional imaging modality 302-2 may capture another type of imagery during a preoperative phase of the surgical procedure.

Imaging data 304 representative of surgical site 306 may include images captured at surgical site 306 by imaging modalities 302. For example, imaging data 304 may include endoscopic images, ultrasound images, CT images, MRI images, and/or any other suitable form of images of surgical site 306. Additionally or alternatively, imaging data 304 may include one or more models of surgical site 306 that are generated based on imaging performed by an imaging modality. For example, additional imaging data 304-2 may include a 3D model of surgical site 306 that is generated based on imaging performed by an imaging modality, such as imaging performed by an ultrasound machine, a CT machine, an MRI machine, or another suitable imaging modality. The 3D model may be a full volumetric model that includes voxels (i.e., volumetric pixels) having values (e.g., color values, brightness values, etc.) representative of an appearance of surgical site 306 at 3D points within the model. Such a volumetric model may facilitate any slice of the 3D model being identified and used by system 100 to produce an image of the slice of the 3D model.

While FIG. 3 depicts two imaging modalities 302-1 and 302-2 respectively capturing imaging data 304-1 and 304-2 that are provided as input to system 100, other examples may include any suitable number and/or configuration of multiple, different imaging modalities that capture imagery that is provided as input to system 100 for use in generating composite imagery of surgical site 306. For example, three or more different imaging modalities may capture imagery that is input to system 100 for use in generating composite imagery of surgical site 306.

System 100 may generate composite imagery 312 (e.g., including one or more composite images 312) of surgical site 306 based on imaging data 304 captured by imaging modalities 302. System 100 may do this in any of the ways described herein to generate a composite image that includes integrated representations of portions of surgical site 306 as captured by different imaging modalities 302. Examples of such composite images and how the composite images may be generated will be described in more detail below.

System 100 may direct a display device 314 to display composite imagery 312. For example, system 100 may provide data representative of composite imagery 312 to display device 314, which may be configured to display composite imagery 312 for viewing by a user of a computer-assisted surgical system (e.g., a surgeon or other surgical team member performing the surgical procedure). Display device 314 may include any device capable of receiving and processing imaging data to display one or more images. To this end, display device 314 may include one or more display screens on which images may be displayed. In certain examples, display device 314 may be a component of or communicatively connected to a computer-assisted surgical system such as will be described in more detail below.

Figure 4:
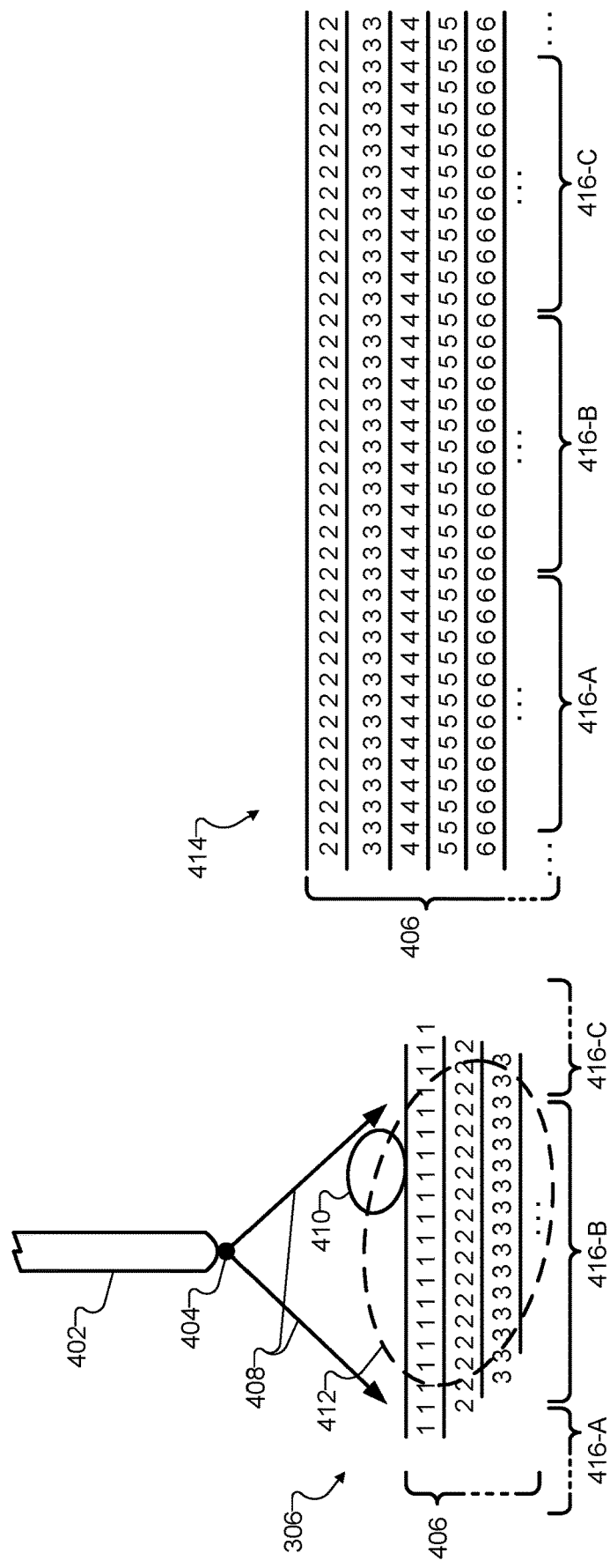
FIG. 4A illustrates exemplary aspects of an endoscopic imaging modality for capturing endoscopic imaging data depicting anatomy at a surgical site according to principles described herein.
FIG. 4B illustrates exemplary aspects of a representation of the surgical site captured by an additional imaging modality distinct from the endoscopic imaging modality illustrated in FIG. 4A according to principles described herein.

FIG. 4A illustrates exemplary aspects of an endoscopic imaging modality for capturing endoscopic imaging data depicting anatomy at a surgical site. More specifically, FIG. 4A shows an exemplary depiction of surgical site 306 as captured with an endoscope 402 that is implemented as any suitable endoscopic instrument and is associated with a viewpoint 404 positioned relative to surgical site 306. While FIG. 4A shows a 2D view, principles described with respect to the 2D view also apply to a 3D view of a surgical site with a viewpoint positioned relative to the surgical site.

As shown in FIG. 4A, surgical site 400 includes anatomy 406, which may include any suitable anatomical structure (e.g., an organ or other tissue) and which is depicted, for illustrative reasons that will become apparent, in various layers or cross sections that indicate relative depth of the anatomy rather than being depicted, for instance, using accurate anatomical detail of an actual internal organ. It will be understood that surface anatomy directly visible to endoscope 402 is labeled with a series of "1s" (i.e., "1 1 1 1 1 1 1 1 . . . ") and may represent the surface anatomy 308 that is shown in FIG. 3 above. Moreover, various cross-sections of subsurface anatomy that are behind or beneath the surface anatomy with respect to viewpoint 404 (and thus are not visible in anatomy 308 of FIG. 3) are labeled with a series of "2s" (i.e., "2 2 2 2 2 2 2 2 2 . . . "), "3s" (i.e., "3 3 3 3 3 3 3 3 3 . . . "), and so forth, based on the relative depth from the surface. Subsurface anatomy may include any portion of anatomy 406 positioned behind the surface anatomy layer labeled with "1s" from the perspective of viewpoint 404 and/or hidden from view from the perspective of viewpoint 404 by the surface anatomy. In certain examples, the surface anatomy may include an outer layer of tissue of a patient, and the subsurface anatomy may include anatomy embedded within the outer layer of tissue.

As shown, viewpoint 404 may be associated with endoscope 402 by, for example, being the viewpoint from which a user of endoscope 402 views surgical site 306 (e.g., the viewpoint of one or more cameras of the endoscope). As such, it will be understood that viewpoint 404 may also serve as a viewpoint from which composite imagery (e.g., composite imagery 312) of surgical site 306 may be rendered. In some examples, rather than being the actual viewpoint of endoscope 402, viewpoint 404 may be a virtual viewpoint corresponding to a viewpoint of another imaging modality other than the endoscopic imaging modality, or may be another arbitrary viewpoint with respect to surgical site 306. Viewpoint 404 may be associated with and/or represent intrinsic and extrinsic properties of an imaging device such as one or more cameras of an endoscope. Viewpoint 404 may have a field of view 408 within which an image of surgical site 306 may be captured by endoscope 402 and/or within which a composite image of surgical site 306 may be rendered.

FIG. 4A further depicts a subsurface imaging module 410 that may be associated with endoscope 402. For example, subsurface imaging module 410 may be implemented as an ultrasound module or another suitable subsurface imaging module described herein. Endoscope 402 and subsurface imaging module 410 may both be controlled by a manipulating system of a computer-assisted surgical system (such as will be described in more detail below), such that the computer-assisted surgical system may track (e.g., using kinematics, visual tracking, etc.) endoscope 402 and subsurface imaging module 410 in a manner that allows the relative location of one to be known with respect to the other. More particularly, the computer-assisted surgical system may generate, track, and maintain alignment parameters representative of a registration of endoscopic imaging data captured by endoscope 402 with subsurface imaging data captured by subsurface imaging module 410.

System 100 may access the alignment parameters that represent the registration of the endoscopic imaging data with the subsurface imaging data. As such, system 100 may accurately determine a location, with respect to viewpoint 404, of any anatomy represented within subsurface imaging data captured by subsurface imaging module 410 (e.g., any anatomy included within a capture field 412 associated with subsurface imaging module 410). As one example, any subsurface structure (e.g., any particular vasculature, particular bone structure, particular tissue mass, etc.) represented within subsurface imaging data representative of anatomy in capture field 412 may be automatically registered to endoscope 402 based on the alignment parameters so that system 100 has updated data indicating the location and geometry of the subsurface structure with respect to viewpoint 404.

While endoscope 402 may be configured to only capture endoscopic imaging data depicting the surface of anatomy 406, and subsurface imaging module 410 may be configured to only capture subsurface imaging data at a particular cross section within capture field 412, various other portions or types of views of anatomy 406 may also be available and of interest to a user performing a procedure at surgical site 306. As mentioned above, some of these additional portions or views of anatomy 406 may be captured by way of other imaging modalities at the same time or at a different time as when endoscope 402 and subsurface imaging module 410 are capturing imaging data. To the extent that such additional imaging data may be accurately registered with the endoscopic and/or subsurface imaging data described in relation to FIG. 4A, it may therefore be desirable for these other anatomical portions or views of anatomy 406 to be presented to the user from viewpoint 404 (e.g., together with the view depicted by the endoscopic imaging data).

To illustrate, FIG. 4B shows exemplary aspects of a representation 414 of anatomy 406 at surgical site 306 that is captured by an additional imaging modality distinct from the endoscopic imaging modality illustrated in FIG. 4A. Because representation 414 may be captured by way of a different imaging modality than the endoscopic imaging data captured by endoscope 402, representation 414 may include data representative of additional portions, views, and insights into anatomy 406. For instance, representation 414 may represent a different or more comprehensive representation (e.g., a 3D model or the like) of anatomy 406 at surgical site 306. Specifically, as shown, FIGS. 4A and 4B each label different portions 416 (e.g., portions 416-A through 416-C), as well as different depths (labeled with "1s", "2s", "3s", etc.) of anatomy 406 at surgical site 306. However, while only portion 416-B and depths labeled with "1s" through "3s" are shown to be imaged by endoscope 402 and subsurface imaging module 410, all of portions 416-A through 416-C together with depths labeled with "2s" through "6s" and beyond (indicated by ellipsis) are shown to be represented within representation 414. (It will be understood that the portions and depths of anatomy 406 shown are of arbitrary size, appearance, and quantity for illustrative purposes and that additional portions and/or depths of any suitable size or appearance may be included in other examples.) As such, representation 414 may not represent the surface of anatomy 406 or may represent the surface anatomy in a different manner than it is represented by the endoscopic imaging data of FIG. 4A such that a direct comparison of surface anatomy features may not be a feasible, efficient, effective, and/or convenient way to register representation 414 with the endoscopic imaging data.

Representation 414 may be implemented as a 3D anatomical model or other such data structure, and may be generated based on additional imaging data captured by way of a non-endoscopic imaging modality. For example, representation 414 may be generated based on CT scan data, MRI scan data, ultrasound scan data, or any other imaging data as may serve a particular embodiment. In some examples, the data upon which representation 414 is based may be captured at a different time than the endoscopic imaging data captured by endoscope 402. For instance, as mentioned above, the endoscopic imaging data may be captured intraoperatively while the additional imaging data may have been captured (and the 3D model of representation 414 generated) preoperatively.

Returning to FIG. 3, endoscopic imaging data 304-1 may be implemented in certain examples by data depicting the surface layer of anatomy 406 (i.e., anatomy 308) as captured by endoscope 402 from viewpoint 404. Additional imaging data 304-2 may refer, in these examples, to data representative of representation 414 (i.e., including subsurface areas of anatomy 406 captured by another imaging modality independent from endoscope 402). As shown, endoscopic imaging data 304-1 and additional imaging data 304-2 may both be accounted for by system 100 to generate or correct a registration of endoscopic imaging data 304-1 with additional imaging data 304-2, and to generate composite imagery 312.

In order to perform this registration, system 100 may identify and match up corresponding aspects of endoscopic imaging data 304-1 and additional imaging data 304-2. However, as mentioned above, while both imaging data 304-1 and 304-2 may represent certain common portions of anatomy 406 such as portion 416-B (albeit in different ways and/or to different extents or with different scope), there may not be any visually identifiable features common to the depiction of endoscopic imaging data 304-1 and representation 414 of additional imaging data 304-2. Accordingly, it may not be feasible, efficient, effective, convenient, or even possible to perform the registration of imaging data 304-1 with imaging data 304-2 by feature matching in the manner described above in relation to FIG. 2.

To illustrate, FIG. 5 shows exemplary aspects of a registration of endoscopic imaging data 304-1 (e.g., captured by way of an endoscopic imaging modality by endoscope 402) with additional imaging data 304-2 (e.g., captured by way of an additional imaging modality distinct from the endoscopic imaging modality). As shown, endoscopic imaging data 304-1 depicts surface anatomy at surgical site 306 (i.e., the portion of anatomy 406 labeled with "1s"). This surface anatomy depiction will be understood to be captured by way of endoscope 402 from viewpoint 404 at surgical site 306. Moreover, FIG. 5 shows additional imaging data 304-2 that represents subsurface anatomy at surgical site 306 (i.e., the portion of anatomy 406 labeled with "2s"). This subsurface anatomy will be understood to be occluded by the surface anatomy from viewpoint 404 such that the subsurface anatomy is not represented within imaging data 304-1.

Accordingly, the depiction of endoscopic imaging data 304-1 in FIG. 5 depicts various "1s" to indicate that the surface layer is depicted, and further shows various surface features 204 representative of the types of features 204 visible on the surface anatomy as described above in relation to FIG. 2. In like manner, the depiction of additional imaging data 304-2 in FIG. 5 depicts various "2s" to indicate that a particular subsurface cross section (e.g., a cross section associated with the depth labeled with "2s" in FIG. 4B) is depicted. It will be understood that, in some examples, additional imaging data 304-2 may include a 3D representation of more than a single cross section. For instance, additional imaging data 304-2 may include a 3D model that incorporates various depths from representation 414.

Regardless of precisely what subsurface portions are represented within additional imaging data 304-2, the depiction of additional imaging data 304-2 in FIG. 5 illustrates that corresponding features 206 (described above in relation to FIG. 2 as corresponding to features 204) may not be present in the representation of additional imaging data 304-2. The "Xs" representative of each feature 206 is shown in FIG. 5 at a location where the features would be located (with respect to viewpoint 404) if present within additional imaging data 304-2, but the "Xs" are drawn with dashed lines to indicate that the features are not present in additional imaging data 304-2. Accordingly, it would not be possible to identify and match up features 204 and 206 in order to register imaging data 304-1 with imaging data 304-2 in this example, and another correlatable characteristic of the respective imaging datasets may need to be identified in order for the registration to be accurately performed.

As has been described, the characteristics used for the registration (e.g., as an alternative to visual features 204 and 206 when visual features 204 and 206 are not both available in the respective imaging data to be registered) may relate to identifiable subsurface structures. For example, such a subsurface structure may be vasculature at the surgical site, non-vasculature anatomy that includes at least one of a bone structure or a tissue mass, or another suitable subsurface structure. Such subsurface structures may be useful for performing registration procedures because, as described above, these subsurface structures may be both 1) detected and registered to endoscopic imaging data 304-1 (e.g., by way of subsurface imaging module 410 and its predefined and tracked relationship to endoscope 402, as described in relation to FIG. 4A), and 2) included within additional imaging data 304-2 due to the presence of the subsurface structures throughout the subsurface anatomy represented by representation 414. To illustrate, a plurality of squares each representing a particular feature of a subsurface structure (e.g., a cross section of a blood vessel, a feature of a bone structure, a feature of a tissue mass, etc.) detectable within both imaging data 304-1 and 304-2 are shown in FIG. 5. In endoscopic imaging data 304-1, the features of the subsurface structures represented by these squares will be referred to individually as features 502-1 through 502-6 and collectively as subsurface structures 502. In additional imaging data 304-2, the corresponding subsurface features represented by the squares will be referred to individually as features 504-1 through 504-6 and collectively as subsurface structures 504.

Subsurface structures 502 may be identified within endoscopic imaging data 304-1 based on subsurface imaging data detected by a subsurface image scan at surgical site 306 by subsurface imaging module 410. For example, subsurface structures 502 may be identified using vascular image scanning (e.g., doppler ultrasound scanning or other types of 2D or 3D vascular image scanning) or other subsurface image scanning described herein to identify and generate data representative of subsurface structures 502. In the example of doppler ultrasound scanning (e.g., where subsurface structures 502 and 504 are implemented by vasculature and each of the features 502-1 through 502-6 and 504-1 through 504-6 are implemented by individual blood vessels), a doppler ultrasound device may employ the doppler principle (e.g., the doppler effect) to detect the flow of fluids in tissue. At locations where doppler ultrasound detects that fluids are moving in a relatively small space through the anatomy, it may be inferred or otherwise determined that a vein, artery, or other blood vessel is present. For example, doppler ultrasound may indicate fluid motion direction by way of different colors (e.g., red or blue) and may overlay such colors on top of (or blend or otherwise integrate such colors into) endoscopic imaging data 304-1 at the locations indicated by the squares representing the blood vessels (i.e., features 502-1 through 502-6). Based on the flow direction, the diameter of different blood vessels, a pattern of how the blood vessels are distributed geometrically, and/or any other suitable criteria, system 100 may differentiate different types of blood vessels (e.g., arteries, veins, etc.) and/or may identify specific blood vessels to be features 502. While vasculature and blood vessels are described in this instance as one specific example, it will be understood that other types of non-vasculature subsurface structures (e.g., bone structures, tissue masses, etc.) may similarly be employed with their corresponding features in a similar way as described for vasculature structures and blood vessel features.

Subsurface structures 504 may be identified within additional imaging data 304-2 based on other methods appropriate to the imaging modality used to capture additional imaging data 304-2. For example, subsurface structures 504 may be identified by data captured in a CT or MRI scan, or in any other suitable manner appropriate for a particular imaging modality being used (such as other imaging modalities described herein). In cases where a comprehensive representation such as a 3D model has been constructed from such data, the representation may include metadata that differentiates different types of subsurface features 504 (e.g., blood vessels, bone or tissue features, etc.) and/or identifies specific subsurface features 504.

System 100 may be configured to use subsurface structures 502 and 504 for registration of endoscopic imaging data 304-1 with additional imaging data 304-2 in any suitable manner. For instance, in certain implementations, the use of identified subsurface structures 502 and 504 for the registration of imaging data 304-1 with imaging data 304-2 may include initially generating the registration by, for example, generating appropriate alignment parameters defining any of the types of spatial transformations described herein between the endoscopic imaging data and the additional imaging data (e.g., rigid transformations, affine transformations, deformable registrations, etc.). In other implementations, or at subsequent times in the same implementations, the use of the identified subsurface structures 502 and 504 for the registration of endoscopic imaging data 304-1 with imaging data 304-2 may include correcting the registration (e.g., a previously generated registration) of endoscopic imaging data 304-1 with additional imaging data 304-2, subsequent to an initial generation of the registration. For example, this may be performed by modifying, adjusting, revising, updating, or otherwise correcting one or more alignment parameters defining a particular spatial transformation from the endoscopic to the additional imaging data.

More particularly, in certain examples, the use of identified subsurface structures 502 and 504 for the registration of endoscopic imaging data 304-1 with additional imaging data 304-2 may be performed by system 100 by: 1) accessing endoscopic imaging data 304-1 from endoscope 402 capturing endoscopic imaging data 304-1; 2) accessing the subsurface imaging data from subsurface imaging module 410 performing the subsurface imaging scan; 3) accessing alignment parameters representative of a registration of endoscopic imaging data 304-1 with the subsurface imaging data; 4) determining, based on the subsurface imaging data and the alignment parameters, a first location, with respect to anatomy 406 as represented by endoscopic imaging data 304-1, of a feature 502 present in the identified subsurface structures; 5) determining a second location, with respect to anatomy 406 as represented by additional imaging data 304-2, of a feature 504 feature that corresponds to (i.e., represents the same feature as) the feature 502; and 6) generates or corrects, based on the first and second locations, the registration of endoscopic imaging data 304-1 with additional imaging data 304-2. The feature 502 present in the identified subsurface structures may represent a blood vessel or other feature in any way. For instance, the feature 502 may be the presence of a particular blood vessel, a specific point on a specific blood vessel (e.g., identified using a bifurcation), a registration of multiple blood vessels (e.g., without necessarily distinguishing between individual blood vessels), or any other identifiable feature relating to one or more blood vessels or other suitable subsurface features. Similarly, the feature 504 corresponding to the feature 502 may be any of the same types of features described above, but as represented in additional imaging data 304-2.

When operations such as these are repeated for several subsurface features, a very accurate registration between imaging data 304-1 and imaging data 304-2 may be achieved. As such, in certain implementations, the correlation of pairs of identified features 502 and 504 features in this way may be the primary or only basis for registration of endoscopic imaging data 304-1 with additional imaging data 304-2.

In other implementations, however, correlations between subsurface structures 502 in endoscopic imaging data 304-1 and subsurface structures 504 in additional imaging data 304-2 may serve as just one factor in a plurality of factors utilized to generate or correct the registration. For instance, in certain examples, correlated subsurface structures (e.g., one particular subsurface feature that is identified within both imaging data 304-1 and 304-2) may serve as an anchor for the registration, and other factors such as other features or data detected by other imaging modalities may also be used to complete the registration in the most effective and accurate manner.

As one example, system 100 may further use identified subsurface structures 502 and 504 for the registration by accessing auxiliary data representative of additional features present at the surgical site and distinct from the subsurface structures. In these implementations, the generating or correcting of the registration includes 1) anchoring an alignment of endoscopic imaging data 304-1 and additional imaging data 304-2 based on the first and second locations and with respect to viewpoint 404, and 2) refining the alignment of endoscopic imaging data 304-1 and additional imaging data 304-2 based on the auxiliary data.

In some such examples, the subsurface structures 502 and 504 may comprise vasculature at the surgical site and the additional features present may be additional, non-vasculature anatomy. In these examples, the blood vessel or vessels (or features thereof) implementing features 502 and 504 that are used for such anchoring may be major blood vessels or groups of vessels (e.g., the hilum of the kidney, etc.), and may be selected as anchor points in any suitable way. For example, vessels may be selected as anchor points automatically based on their size in relation to other identified blood vessels (e.g., the selected blood vessels may be the largest), their importance in relation to other identified blood vessels, the ease with which they are uniquely identified in relation to other blood vessels, and/or based on other suitable criteria. In other examples, rather than an automatic selection of blood vessels to be used as anchoring points, system 100 may rely on a manual designation. Specifically, for example, the use of the identified vasculature for the registration of endoscopic imaging data 304-1 with additional imaging data 304-2 may include system 100 detecting a user selection (e.g., by a surgeon or other user by way of an interactive user interface or the like) of a particular blood vessel of the identified vasculature that is to be used as an anchor point. The determining of the first and/or second locations of the particular blood vessel may then be performed based on the detected user selection of the particular blood vessel. Once a selected blood vessel is used to anchor the registration (e.g., once one particular blood vessel is aligned with a corresponding blood vessel), the registration may be further worked out in relation to other degrees of freedom in order to fully align and register the image datasets based on other, non-vasculature-related data (e.g., visible features, other ultrasound data besides the vascular imaging data, etc.).

In other examples employing non-vasculature subsurface structures such as bone structures or tissue masses, the use of the identified subsurface structure for the registration of endoscopic imaging data 304-1 with additional imaging data 304-2 may include system 100 similarly detecting a user selection (e.g., by a surgeon or other user by way of an interactive user interface or the like) of a particular feature of the identified subsurface structure that is to be used as an anchor point. The determining of the first and/or second locations of the particular feature may then be performed based on the detected user selection of the particular feature. Again, once a selected feature is used to anchor the registration (e.g., once one particular feature of the subsurface structure is aligned with a corresponding feature in the other imaging data view), the registration may be further worked out in relation to other degrees of freedom in order to fully align and register the image datasets based on additional features (e.g., surface anatomy features, other subsurface anatomy features visible in a subsurface imaging scan, etc.).

One example of an additional feature upon which the registration refinement may be based is a cautery mark that is applied by a surgeon onto surface anatomy to mark an anatomical region in preparation for an operation. For example, the surgeon may use a cautery instrument to apply one or more cautery marks (i.e., burn marks) outlining or otherwise demarcating an area upon which an operation is to be performed (e.g., marking boundaries of a tissue mass that is to be removed, etc.). Such cautery marks may be readily identifiable in endoscopic imaging data 304-1, and may be associated in a predefined way with anatomy that is readily identifiable within additional imaging data 304-2 (e.g., a tissue mass, a bone structure, etc.). As such, these marks may be useful in certain implementations for refining a registration that has already been anchored using the subsurface structures described herein.

As was described above in relation to FIG. 3, once system 100 accurately registers endoscopic imaging data 304-1 with additional imaging data 304-2, system 100 may generate, based on the registration, one or more composite images (e.g., a composite image sequence or video) showing a depiction of anatomy 406 derived from endoscopic imaging data 304-1 together with a view of anatomy 406 as represented in additional imaging data 304-2. System 100 may provide the composite image of surgical site 306 for display by a display device used by a user such as a surgeon or other surgical team member.

Figure 6:
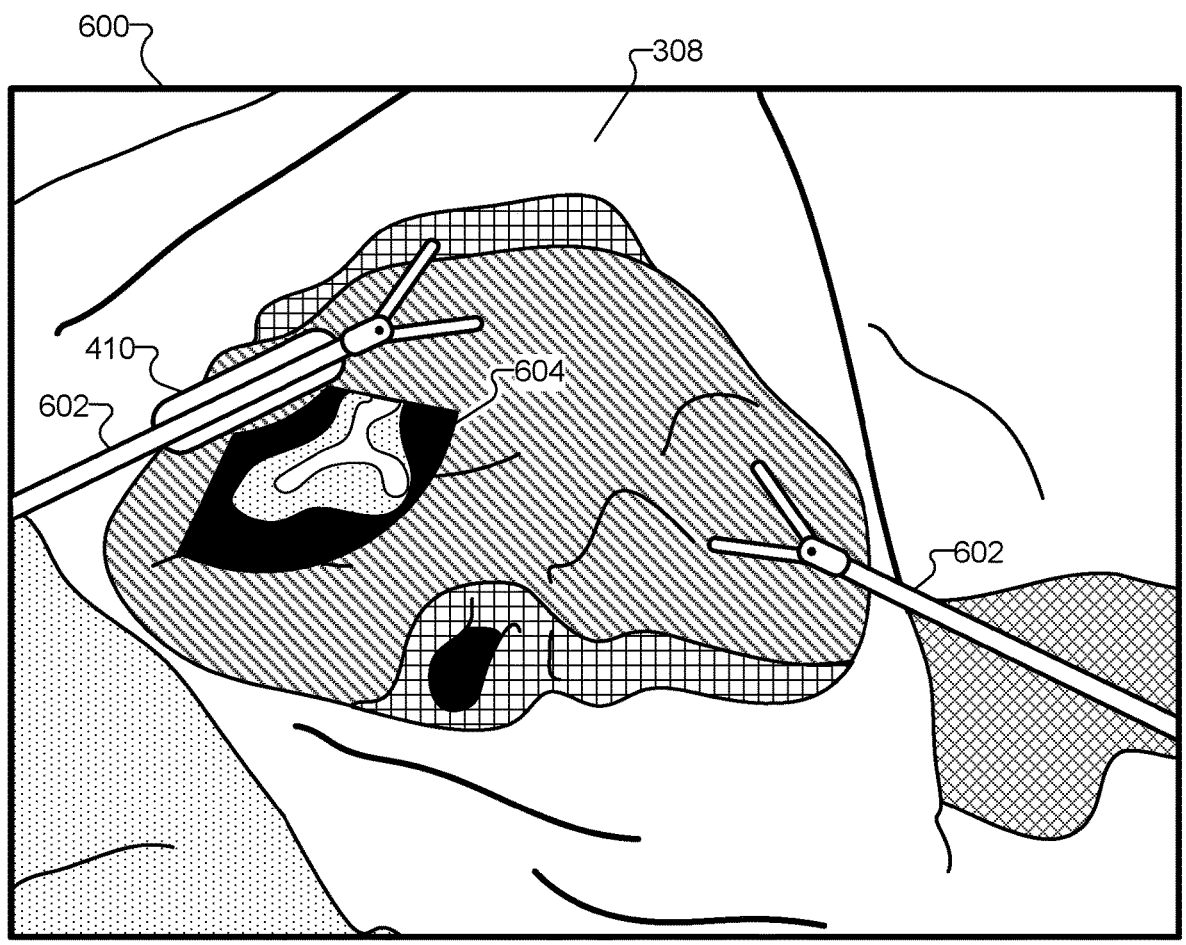
FIGS. 6 through 9 illustrate various exemplary composite images of a surgical site that include depictions of anatomy captured by different imaging modalities and aligned within the composite image with respect to a viewpoint according to principles described herein.

To illustrate, FIG. 6 shows an exemplary composite image 600 of a surgical site such as surgical site 306. Composite image 600 may be primarily composed of an endoscopic image (e.g., a real-time endoscopic image feed) captured by endoscope 402 from the perspective of viewpoint 404 (e.g., endoscopic imaging data 304-1). As such, FIG. 6 shows that most of composite image 600 depicts anatomy 308 (e.g., the surface anatomy portions of anatomy 406) and other elements present at surgical site 306 such as instruments 602 and subsurface imaging module 410. As a composite image, however, image 600 shows more than just the image captured by way of the endoscopic imaging modality. Specifically, as shown, composite image 600 further includes an image augmentation 604 implemented as an overlay or other augmentation (e.g., a blended or integrated augmentation) and comprising a representation (e.g., a cross-section depiction, a 3D model, etc.) of additional imaging data 304-2 captured by way of the additional imaging modality. For example, the depiction of image augmentation 604 may represent a cross section captured by an ultrasound scan (e.g., a preoperative or intraoperative ultrasound scan), a portion of a 3D model generated based on data from a CT scan or an MRI scan, an image derived from a fluoroscopic scan or an x-ray scan, or any other suitable imagery from any suitable imaging modality as described herein or as may serve a particular implementation. Regardless of what type of imagery is shown in image augmentation 604 or what imaging modality is used to capture it, the imagery in image augmentation 604 may show subsurface anatomy that is not detectable (e.g., visible) to the endoscope, and that is properly aligned with viewpoint 404 of the endoscope (e.g., as a result of the registration described above) so as to be located where it would be if the imagery were detectable to the endoscope. As such, a viewer of composite image 600 may perceive image augmentation 604 as a "window" to see through the surface anatomy to a desired view of subsurface anatomy beneath the surface.

Along with the imagery detected by the endoscope (e.g., anatomy 308, instruments 602, etc.) and image augmentation 604, composite image may also show other imagery or information in certain implementations (not explicitly shown in the example of FIG. 6). For example, subsurface imaging data (e.g., red or blue doppler ultrasound spots representative of blood vessels 502, etc.), additional image augmentations depicting similarly aligned subsurface anatomy captured by way of other additional imaging modalities, status information, and/or any other suitable data or imagery may be displayed in composite image 600 as may serve a particular implementation.

In some examples, system 100 may perform certain functions or checks prior to including image augmentation 604 in composite image 600. For instance, system 100 may validate the subsurface imaging data as subsurface imaging module 410 performs the subsurface image scan to provide the subsurface imaging data (e.g., by ensuring that the subsurface imaging module is making proper contact with anatomy 308 to get a good reading if applicable, etc.). Accordingly, system 100 may use the identified subsurface structure for the registration of endoscopic imaging data 304-1 with additional imaging data 304-2 based on the validating of the subsurface imaging data. For example, for a subsurface imaging scan using an ultrasound module that requires contact with the tissue to function properly, system 100 may only generate the registration once contact is made for the first time, may only correct the registration each time contact is made anew, and so forth.

FIG. 6 shows that composite image 600 of surgical site 306 includes a first depiction of anatomy 406 represented by endoscopic imaging data 304-1 (i.e., surface anatomy 308) integrated with a second depiction of anatomy 406 represented by additional imaging data 304-2 (i.e., subsurface anatomy), where the first and second depictions are aligned within the composite image with respect to a viewpoint (e.g., viewpoint 404) that is associated with composite image 600. As mentioned above, however, it will be understood that the identified subsurface structures 502 and 504 that are used for the registration of endoscopic imaging data 304-1 with additional imaging data 304-2 are independent of (i.e., may or may not be the same as or have a relation to) the anatomy in the first and second depictions included in composite image 600. Indeed, while the very subsurface structures 502 and 504 that are used for the registration may be depicted (e.g., as doppler ultrasound colors, as vasculature 3D models, etc.) in composite image 600 for certain examples, different subsurface structures or no subsurface structures at all may be shown in other examples of composite image 600. More specifically, for any given implementation of system 100 and based on circumstances of the surgical operation, surgeon preferences, etc., composite image 600 may or may not display subsurface imaging data as an augmentation (e.g., an image overlay), may or may not show the same area of a 3D model represented by additional imaging data 304-2 as the area being used for the registration, may or may not show the same subsurface depth level as the level at which the subsurface imaging data detects a cross section upon which the registration is based, and so forth.

Figure 7:
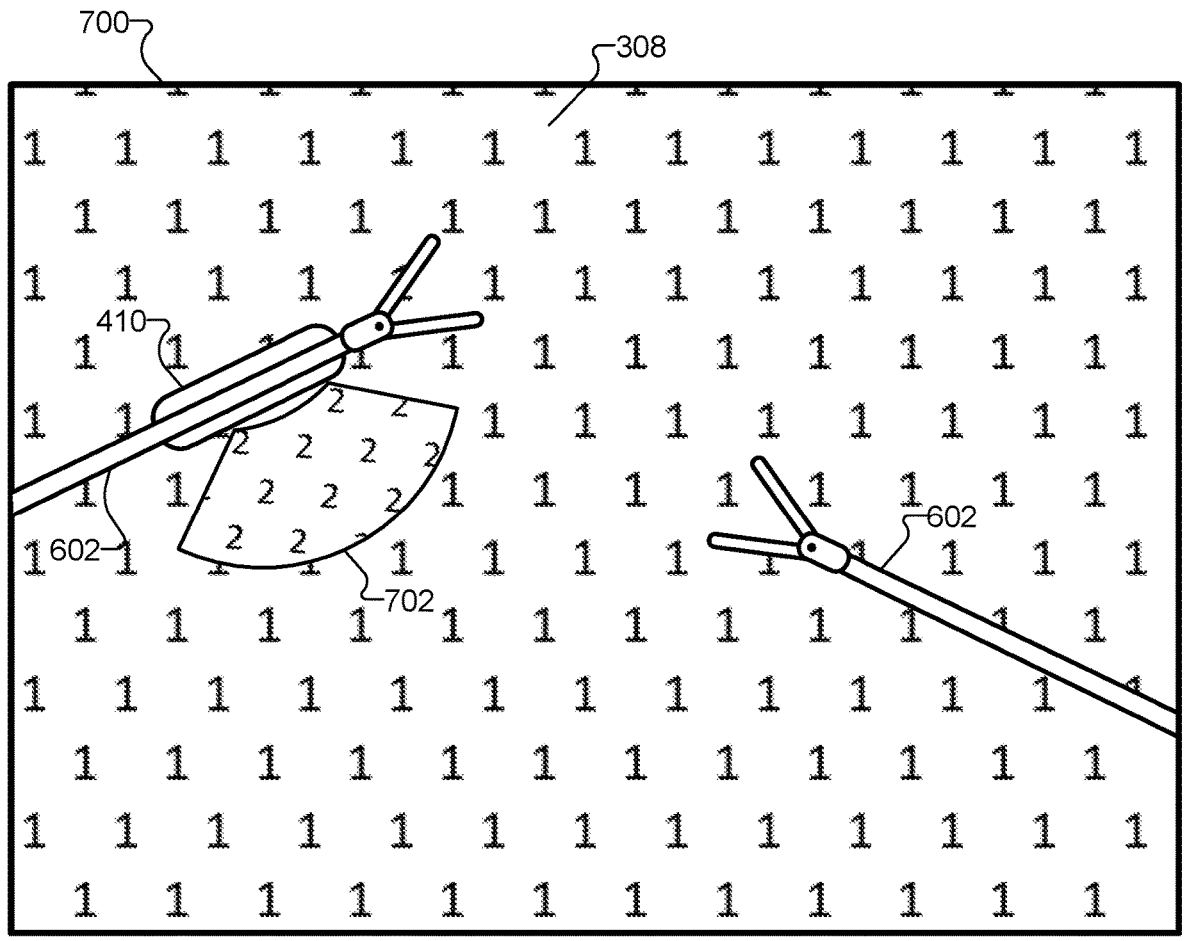
Figure 8:
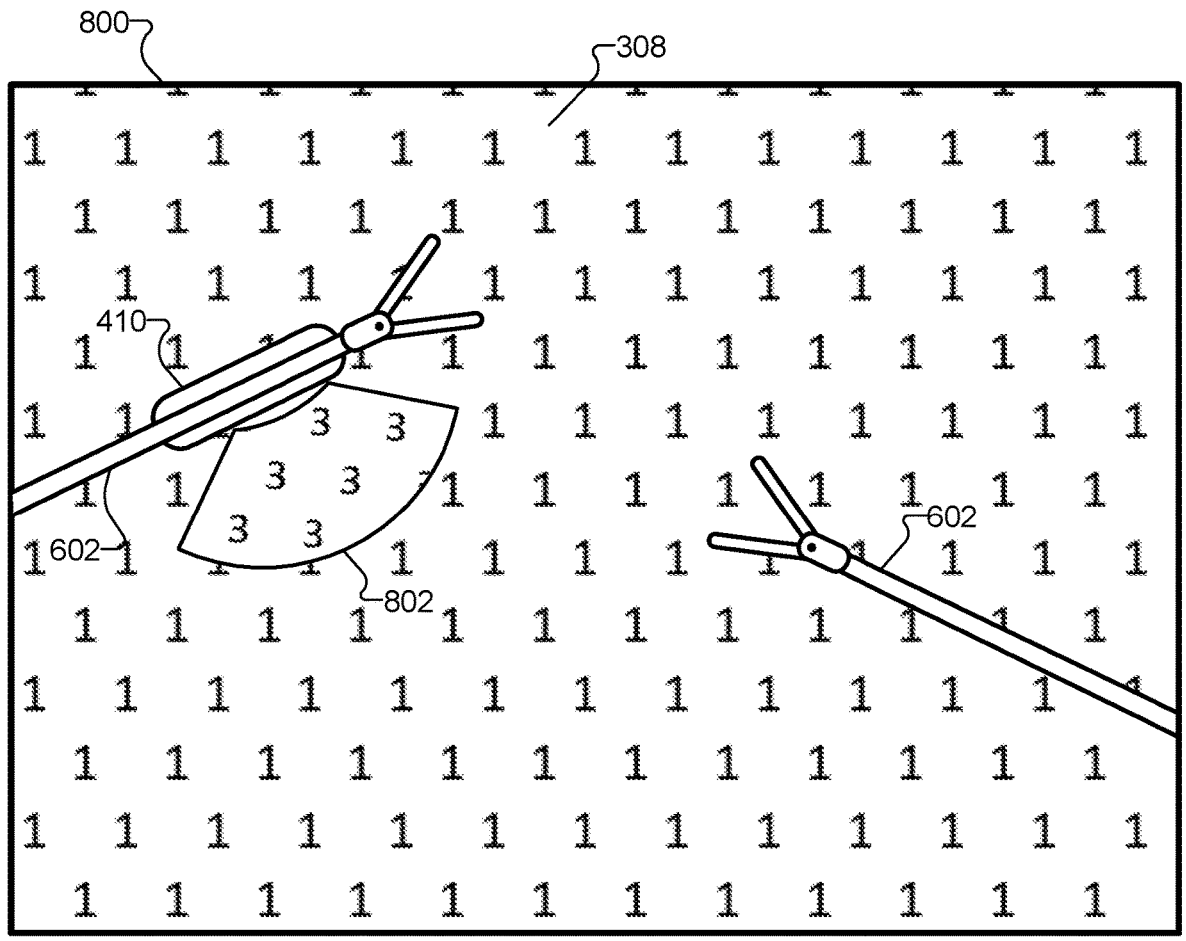
Figure 9:
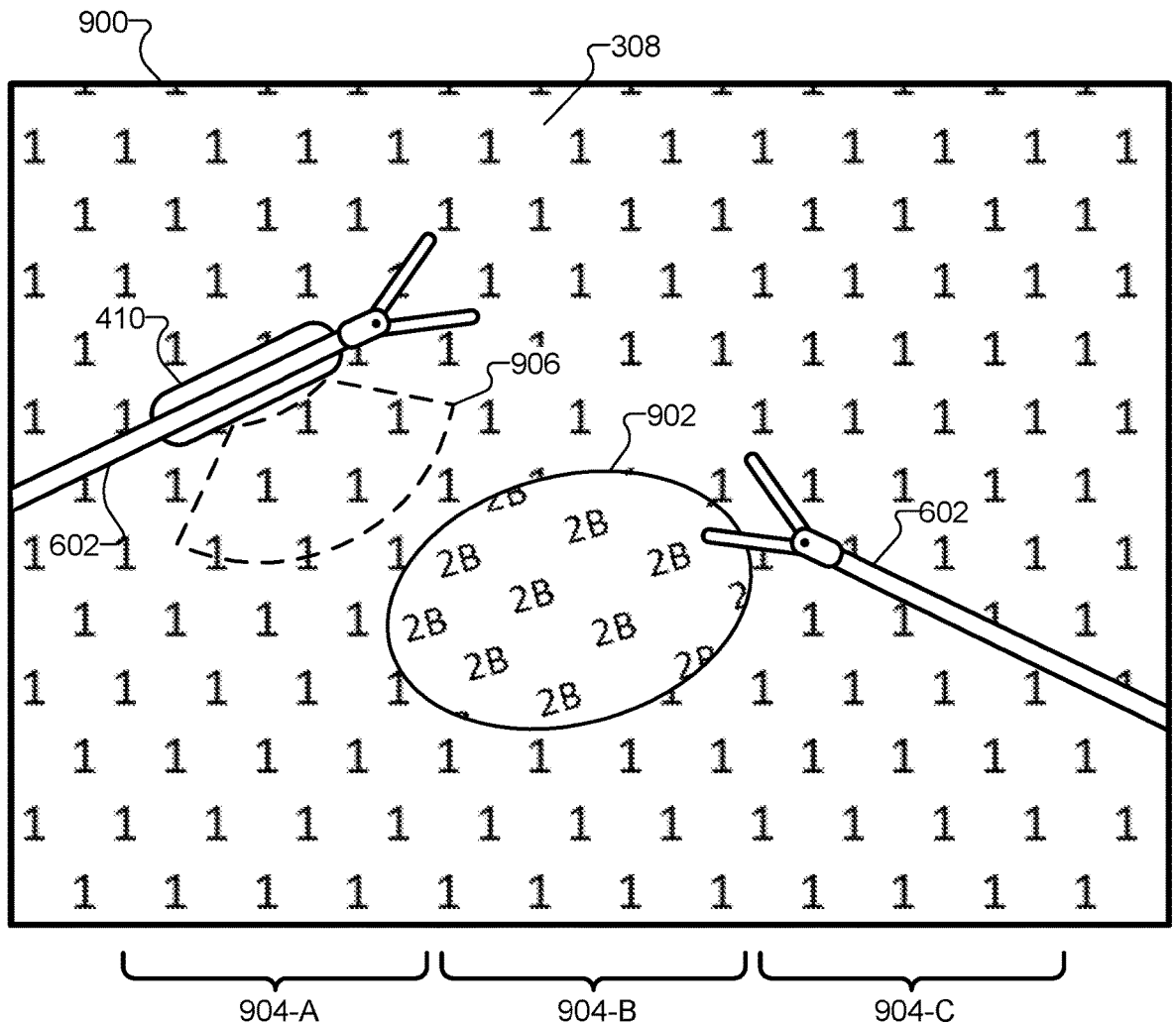

To illustrate, FIGS. 7 through 9 show additional exemplary composite images of surgical site 306 that each include depictions of anatomy 406 that are captured by different imaging modalities and are aligned, within the respective composite images, with respect to a viewpoint associated with the images. In each of FIGS. 7 through 9, the imagery shown in the respective image augmentations is different in order to illustrate the independence the image augmentation can have with the registration of the image data. For clarity, FIGS. 7 through 9 show anatomy portions and depths based on the numbering scheme introduced above in relation to FIGS. 4A and 4B.

FIG. 7 illustrates a composite image 700 that depicts surface anatomy 308 (represented by "1s") at the surgical site, instruments 602, subsurface imaging module 410, and an image augmentation 702. Image augmentation 702 may be any suitable shape including the exemplary shape shown, and may be made to appear to attach to an instrument 602 or to subsurface imaging module 410 (e.g., in a manner analogous to a flag attaching to a flagpole), as shown. In this example, image augmentation 702 depicts subsurface anatomy at the depth represented by "2s," which, as described above, may be the same level at which subsurface imaging module 410 provides a cross section view of subsurface structures 502 that are used to register additional imaging data of image augmentation 702 with the endoscopic imaging data depicting anatomy 308.

Similar to FIG. 7, FIG. 8 shows a composite image 800 that also depicts surface anatomy 308 (represented by "1s") at the surgical site, instruments 602, and subsurface imaging module 410, and that also may be generated based on a registration that uses subsurface imaging data representative of anatomy at the depth represented by "2s". However, in contrast to composite image 700 of FIG. 7, composite image 800 shows an image augmentation 802 that depicts different subsurface anatomy than that used for the registration, namely subsurface anatomy at a depth represented by "3s".

Similar to FIGS. 7 and 8, FIG. 9 shows a composite image 900 that also depicts surface anatomy 308 (represented by "1s") at the surgical site, instruments 602, and subsurface imaging module 410, and that also may be generated based on a registration that uses subsurface imaging data representative of anatomy at a same portion of the surgical site where subsurface imaging module 410 is located. However, in contrast to composite image 700 of FIG. 7 and composite image 800 of FIG. 8, composite image 900 shows an image augmentation 902 that is a different shape and that depicts subsurface anatomy at a different portion 904 than where the subsurface imaging data for the registration is scanned (i.e., a different portion 904 than is scanned by subsurface imaging module 410). Specifically, if the area of the surgical site depicted in composite image 900 is divided roughly into different portions 904 (i.e., portions 904-A through 904-C), it may be seen that subsurface imaging module 410 and an area 906 of anatomy that is scanned during the subsurface image scan are located in portion 904-A, while image augmentation 902 is displayed within a different portion, portion 904-B. Accordingly, to indicate both the depth and the portion being shown in image augmentation 902, "2Bs" are shown to indicate depth "2" and portion 904-B.

As has been mentioned, system 100 may be implemented in or communicatively coupled to a computer-assisted surgical system. System 100 may receive input from and provide output to the computer-assisted surgical system. For example, system 100 may access imagery of a surgical site and/or any information about the surgical site and/or the computer-assisted surgical system from the computer-assisted surgical system, use the accessed imagery and/or information to perform any of the processing described herein to generate composite imagery of the surgical site, and provide data representative of the composite imagery to the computer-assisted surgical system for display (e.g., by a display device associated with the computer-assisted surgical system).

Figure 10:
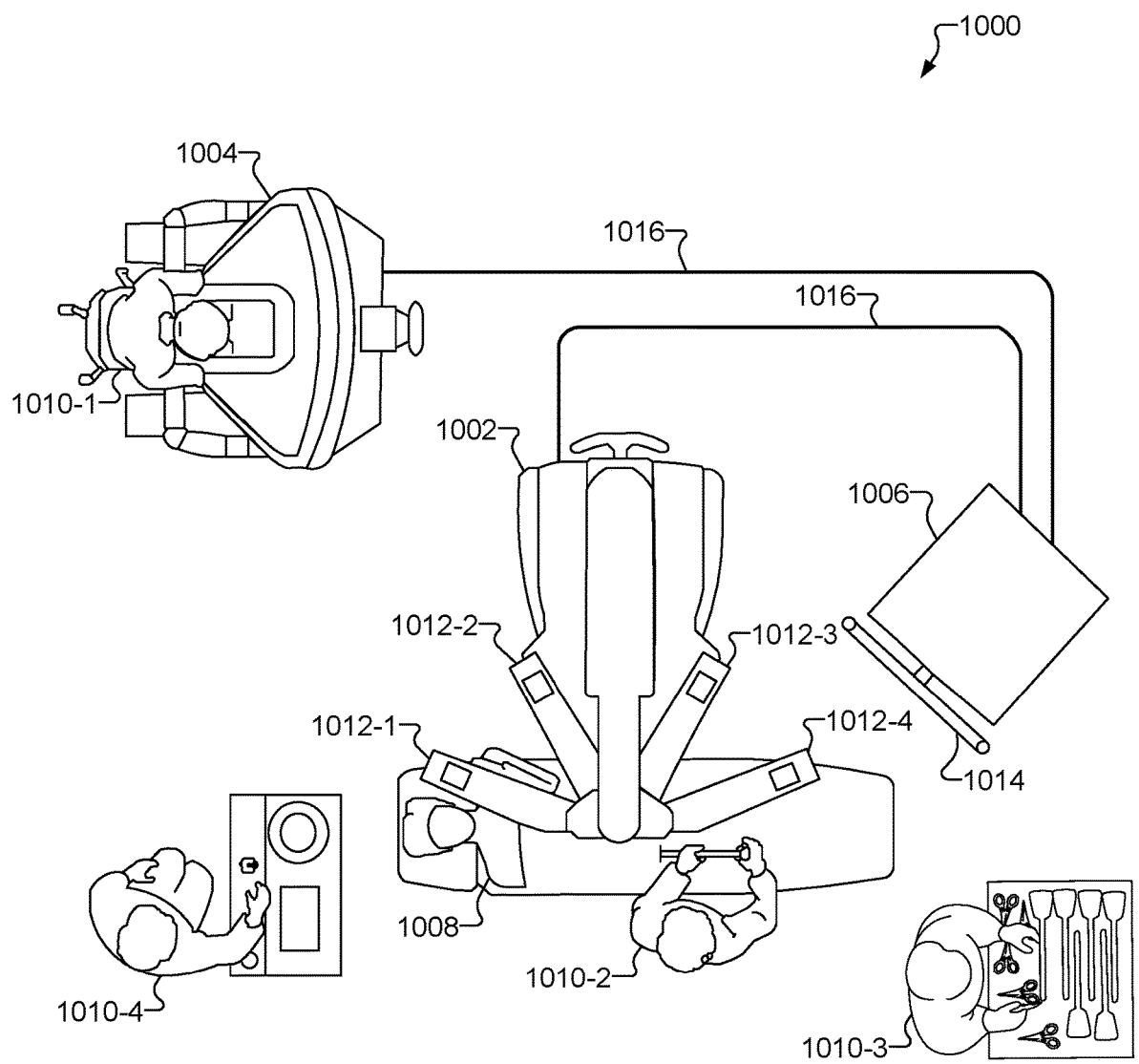
FIG. 10 illustrates an exemplary computer-assisted surgical system according to principles described herein.

To illustrate, FIG. 10 shows an exemplary computer-assisted surgical system 1000 ("surgical system 1000"). System 100 may be implemented by surgical system 1000, connected to surgical system 1000, and/or otherwise used in conjunction with surgical system 1000.

As shown, surgical system 1000 may include a manipulating system 1002, a user control system 1004, and an auxiliary system 1006 communicatively coupled one to another. Surgical system 1000 may be utilized by a surgical team to perform a computer-assisted surgical procedure on a patient 1008. As shown, the surgical team may include a surgeon 1010-1, an assistant 1010-2, a nurse 1010-3, and an anesthesiologist 1010-4, all of whom may be collectively referred to as "surgical team members 1010." Additional or alternative surgical team members may be present during a surgical session as may serve a particular implementation.

While FIG. 10 illustrates an ongoing minimally invasive surgical procedure, it will be understood that surgical system 1000 may similarly be used to perform open surgical procedures or other types of surgical procedures that may similarly benefit from the accuracy and convenience of surgical system 1000. Additionally, it will be understood that the surgical session throughout which surgical system 1000 may be employed may not only include an operative phase of a surgical procedure, as is illustrated in FIG. 10, but may also include preoperative, postoperative, and/or other suitable phases of the surgical procedure.

As shown in FIG. 10, manipulating system 1002 may include a plurality of manipulator arms 1012 (e.g., manipulator arms 1012-1 through 1012-4) to which a plurality of surgical instruments (e.g., such as instruments 602, shown above) may be coupled. Each surgical instrument may be implemented by any suitable surgical tool (e.g., a tool having tissue-interaction functions), medical tool, imaging device (e.g., an endoscope, an ultrasound tool, etc.), sensing instrument (e.g., a force-sensing surgical instrument), diagnostic instrument, or the like that may be used for a computer-assisted surgical procedure on patient 1008 (e.g., by being at least partially inserted into patient 1008 and manipulated to perform a computer-assisted surgical procedure on patient 1008). In some examples, a surgical instrument may be implemented by an ultrasound module (e.g., ultrasound module 410) or such an ultrasound module may be connected to or coupled with one of the other surgical instruments described above. While manipulating system 1002 is depicted and described herein as including four manipulator arms 1012, it will be recognized that manipulating system 1002 may include only a single manipulator arm 1012 or any other number of manipulator arms as may serve a particular implementation.

Manipulator arms 1012 and/or surgical instruments attached to manipulator arms 1012 may include one or more displacement transducers, orientational sensors, and/or positional sensors used to generate raw (i.e., uncorrected) kinematics information. One or more components of surgical system 1000 may be configured to use the kinematics information to track (e.g., determine positions of) and/or control the surgical instruments (as well as anything connected to the instruments such as an ultrasound module).

User control system 1004 may be configured to facilitate control by surgeon 1010-1 of manipulator arms 1012 and surgical instruments attached to manipulator arms 1012. For example, surgeon 1010-1 may interact with user control system 1004 to remotely move or manipulate manipulator arms 1012 and the surgical instruments. To this end, user control system 1004 may provide surgeon 1010-1 with imagery (e.g., high-definition 3D imagery including composite images such as images 600, 700, 800, or 900 or other suitable composite images) of a surgical site associated with patient 1008 as captured by an imaging system (e.g. any of the medical imaging systems described herein). In certain examples, user control system 1004 may include a stereo viewer having two displays where stereoscopic images of a surgical site associated with patient 1008 and generated by a stereoscopic imaging system may be viewed by surgeon 1010-1. In certain examples, composite imagery generated by system 100 may be displayed by user control system 1004. Surgeon 1010-1 may utilize the imagery displayed by user control system 1004 to perform one or more procedures with one or more surgical instruments attached to manipulator arms 1012.

To facilitate control of surgical instruments, user control system 1004 may include a set of master controls. These master controls may be manipulated by surgeon 1010-1 to control movement of surgical instruments (e.g., by utilizing robotic and/or teleoperation technology). The master controls may be configured to detect a wide variety of hand, wrist, and finger movements by surgeon 1010-1. In this manner, surgeon 1010-1 may intuitively perform a procedure using one or more surgical instruments.

Auxiliary system 1006 may include one or more computing devices configured to perform primary processing operations of surgical system 1000. In such configurations, the one or more computing devices included in auxiliary system 1006 may control and/or coordinate operations performed by various other components (e.g., manipulating system 1002 and user control system 1004) of surgical system 1000. For example, a computing device included in user control system 1004 may transmit instructions to manipulating system 1002 by way of the one or more computing devices included in auxiliary system 1006. As another example, auxiliary system 1006 may receive (e.g., from manipulating system 1002) and may process image data representative of imagery captured by an imaging device attached to one of manipulator arms 1012.

In some examples, auxiliary system 1006 may be configured to present visual content to surgical team members 1010 who may not have access to the images provided to surgeon 1010-1 at user control system 1004. To this end, auxiliary system 1006 may include a display monitor 1014 configured to display one or more user interfaces, such as images (e.g., 2D images, 3D images, composite images such as images 600, 700, 800, 900, etc.) of the surgical site, information associated with patient 1008 and/or the surgical procedure, and/or any other visual content as may serve a particular implementation. For example, display monitor 1014 may display images of the surgical site (e.g., composite images generated by system 100) together with additional content (e.g., graphical content, contextual information, etc.) concurrently displayed with the images. In some embodiments, display monitor 1014 is implemented by a touchscreen display with which surgical team members 1010 may interact (e.g., by way of touch gestures) to provide user input to surgical system 1000.

Manipulating system 1002, user control system 1004, and auxiliary system 1006 may be communicatively coupled one to another in any suitable manner. For example, as shown in FIG. 10, manipulating system 1002, user control system 1004, and auxiliary system 1006 may be communicatively coupled by way of control lines 1016, which may represent any wired or wireless communication link as may serve a particular implementation. To this end, manipulating system 1002, user control system 1004, and auxiliary system 1006 may each include one or more wired or wireless communication interfaces, such as one or more local area network interfaces, Wi-Fi network interfaces, cellular interfaces, etc.

Figure 11:
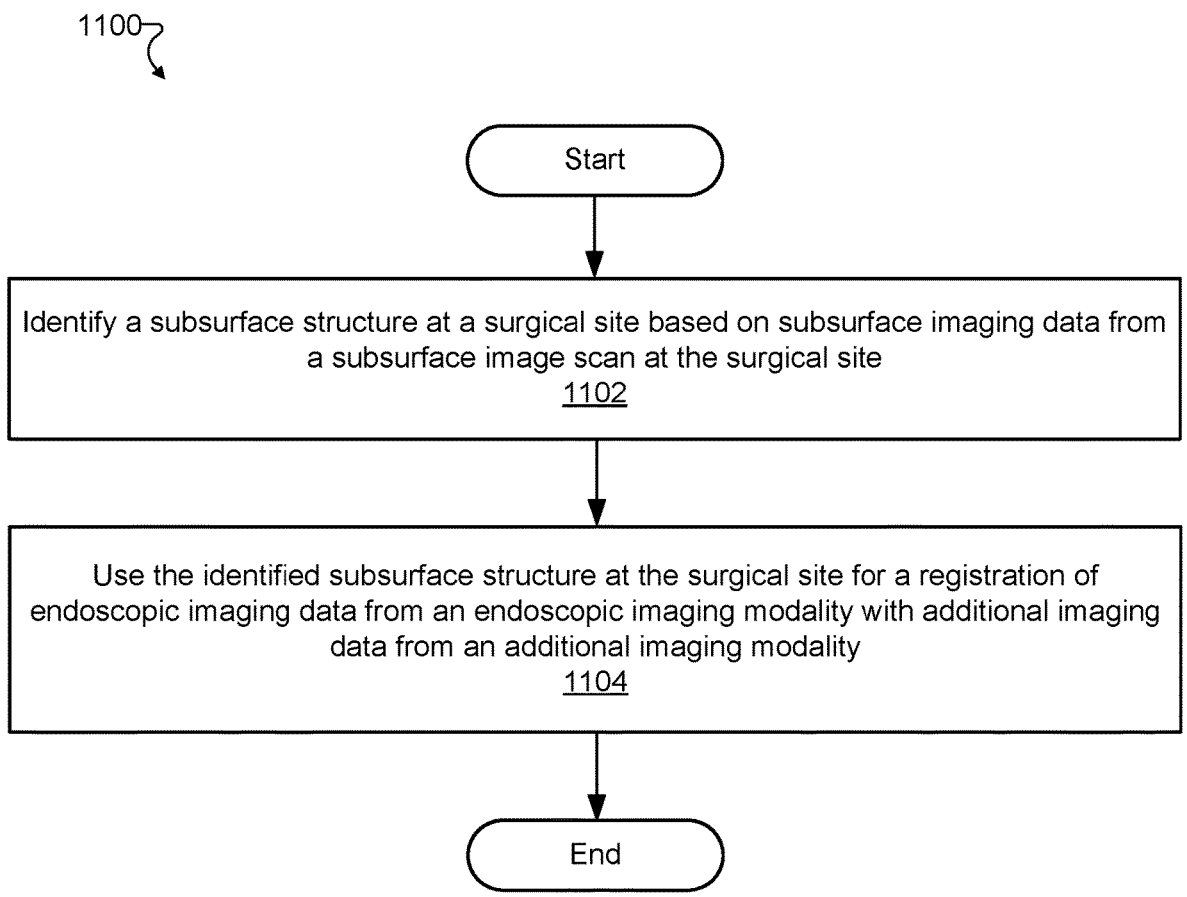
FIGS. 11 and 12 illustrate exemplary methods for registering imaging data from different imaging modalities based on subsurface image scanning according to principles described herein.

FIG. 11 illustrates an exemplary method 1100 for registering imaging data from different imaging modalities based on subsurface image scanning. While FIG. 11 illustrates exemplary operations according to one embodiment, other embodiments may omit, add to, reorder, combine, and/or modify any of the operations shown in FIG. 11. One or more of the operations shown in in FIG. 11 may be performed by an image registration system such as system 100, any components included therein, and/or any implementation thereof.

In operation 1102, an image registration system may identify a subsurface structure at a surgical site based on subsurface imaging data from a subsurface image scan at the surgical site. Operation 1102 may be performed in any of the ways described herein.

In operation 1104, the image registration system may use the subsurface structure identified in operation 1102 for a registration of endoscopic imaging data from an endoscopic imaging modality with additional imaging data from an additional imaging modality. Operation 1104 may be performed in any of the ways described herein.

Figure 12:
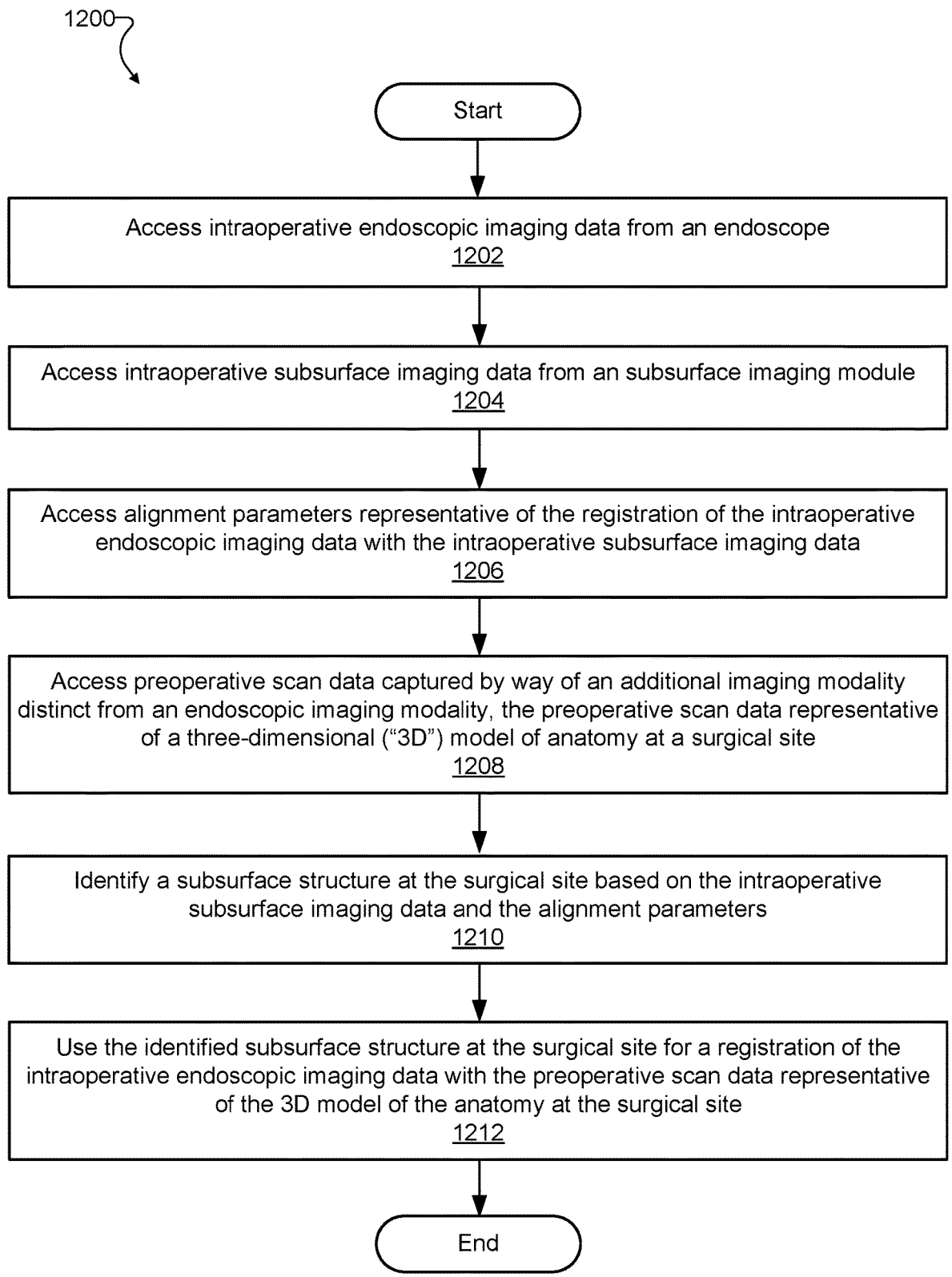

FIG. 12 illustrates another exemplary method, a method 1200, for registering imaging data from different imaging modalities based on subsurface image scanning. While FIG. 12 illustrates exemplary operations according to one embodiment, other embodiments may omit, add to, reorder, combine, and/or modify any of the operations shown in FIG. 12. One or more of the operations shown in FIG. 12 may be performed by an image registration system such as system 100, any components included therein, and/or any implementation thereof.

In operation 1202, an image registration system may access intraoperative endoscopic imaging data from an endoscope associated with the image registration system. For example, the endoscope may be configured to capture the intraoperative endoscopic imaging data. Operation 1202 may be performed in any of the ways described herein.

In operation 1204, the image registration system may access intraoperative subsurface imaging data from a subsurface imaging module associated with the image registration system. For example, the subsurface imaging module may be configured to capture the intraoperative subsurface imaging data. Operation 1204 may be performed in any of the ways described herein.

In operation 1206, the image registration system may access alignment parameters representative of a registration of the intraoperative endoscopic imaging data with the intraoperative subsurface imaging data. Operation 1206 may be performed in any of the ways described herein.

In operation 1208, the image registration system may access preoperative scan data. For example, the preoperative scan data may be captured by way of an additional imaging modality distinct from an endoscopic imaging modality, and the preoperative scan data may be representative of a 3D model of anatomy at the surgical site. Operation 1208 may be performed in any of the ways described herein.

In operation 1210, the image registration system may identify a subsurface structure at the surgical site. For example, the image registration system may identify the subsurface structure based on the intraoperative subsurface imaging data and the alignment parameters. Operation 1210 may be performed in any of the ways described herein.

In operation 1212, the image registration system may use the subsurface structure identified in operation 1210 for a registration of the intraoperative endoscopic imaging data accessed in operation 1202 with the preoperative scan data accessed in operation 1208 and representative of the 3D model of the anatomy at the surgical site. Operation 1212 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 13:
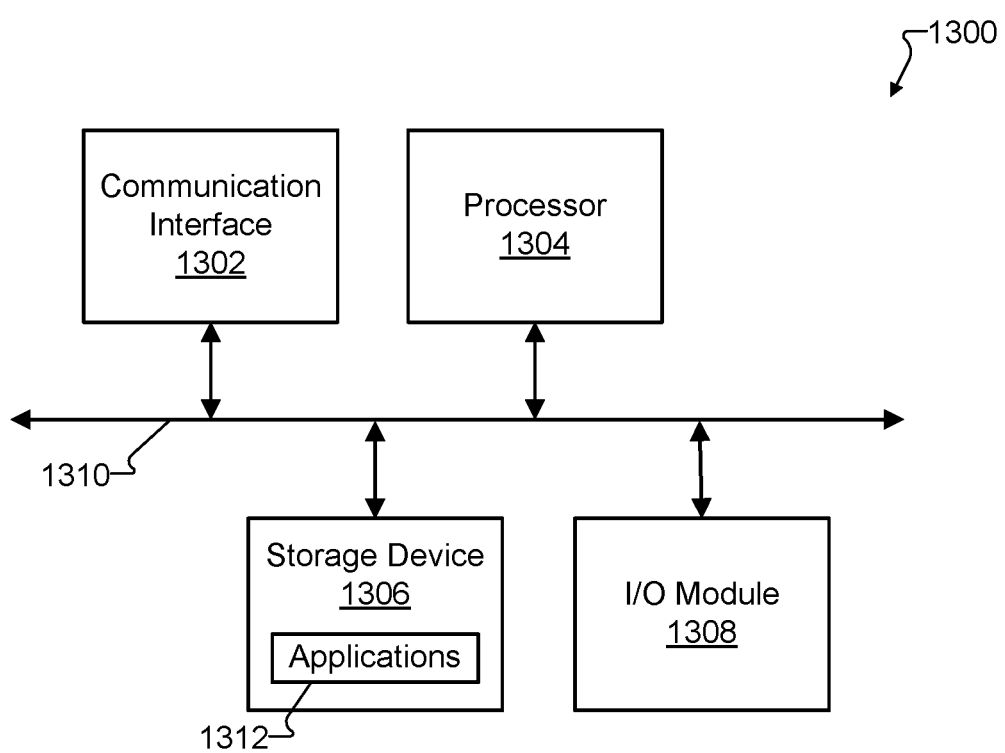
FIG. 13 illustrates an exemplary computing device according to principles described herein.

FIG. 13 illustrates an exemplary computing device 1300 that may be specifically configured to perform one or more of the processes described herein. Any of the systems, units, computing devices, and/or other components described herein may be implemented by computing device 1300.

As shown in FIG. 13, computing device 1300 may include a communication interface 1302, a processor 1304, a storage device 1306, and an input/output ("I/O") module 1308 communicatively connected one to another via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data and/or interpreting, executing, and/or directing execution of one or more of the instructions, processes, and/or operations described herein. Processor 1304 may perform operations by executing computer-executable instructions 1312 (e.g., an application, software, code, and/or other executable data instance) stored in storage device 1306.

Storage device 1306 may include one or more data storage media, devices, or configurations and may employ any type, form, and combination of data storage media and/or device. For example, storage device 1306 may include, but is not limited to, any combination of the non-volatile media and/or volatile media described herein. Electronic data, including data described herein, may be temporarily and/or permanently stored in storage device 1306. For example, data representative of computer-executable instructions 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1300. For example, one or more applications 1312 residing within storage device 1306 may be configured to direct an implementation of processor 1304 to perform one or more operations or functions associated with processing facility 104 of system 100. Likewise, storage facility 102 of system 100 may be implemented by or within an implementation of storage device 1306.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
  a memory storing instructions; and
  a processor communicatively coupled to the memory and configured to execute the instructions to:
    identify a differentiated set of blood vessels differentiated from other blood vessels at a surgical site based on subsurface imaging data from a subsurface image scan at the surgical site; and
    use the differentiated set of blood vessels identified at the surgical site for a registration of endoscopic imaging data from an endoscopic imaging modality with additional imaging data from an additional imaging modality,
wherein the using of the differentiated set of blood vessels identified at the surgical site for the registration of the endoscopic imaging data with the additional imaging data includes:
determining, based on the subsurface imaging data and alignment parameters representative of a registration of the endoscopic imaging data with the subsurface imaging data, a first location, with respect to anatomy as represented by the endoscopic imaging data, of the differentiated set of blood vessels identified at the surgical site;
determining a second location, with respect to the anatomy as represented by the additional imaging data, of the differentiated set of blood vessels; and
generating or correcting, based on the first and second locations, the registration of the endoscopic imaging data with the additional imaging data.

2. The system of claim 1, wherein the processor is further configured to execute the instructions to provide a composite image of the surgical site, for display by a display device, based on the registration of the endoscopic imaging data from the endoscopic imaging modality with the additional imaging data from the additional imaging modality.

3. The system of claim 2, wherein:
the composite image of the surgical site includes a first depiction of anatomy represented by the endoscopic imaging data integrated with a second depiction of anatomy represented by the additional imaging data, the first and second depictions aligned within the composite image with respect to a viewpoint associated with the composite image; and
the differentiated set of blood vessels identified at the surgical site and used for the registration is distinct from the anatomy in the first and second depictions included in the composite image.

4. The system of claim 1, wherein:
the endoscopic imaging data depicts surface anatomy at the surgical site, the surface anatomy depiction captured by way of the endoscopic imaging modality from a viewpoint at the surgical site; and
the additional imaging data represents subsurface anatomy at the surgical site, the subsurface anatomy occluded by the surface anatomy from the viewpoint such that the subsurface anatomy is not represented within the endoscopic imaging data.

5. The system of claim 1, wherein:
the endoscopic imaging modality comprises an intraoperative scan of anatomy at the surgical site; and
the additional imaging modality comprises a preoperative scan of the anatomy at the surgical site.

6. The system of claim 1, wherein the additional imaging modality comprises one of:
an ultrasound scan of the surgical site;
a computerized tomography ("CT") scan of the surgical site;
a magnetic resonance imaging ("MRI") scan of the surgical site; or
a fluoroscopic imaging scan of the surgical site.

7. The system of claim 1, wherein the using of the differentiated set of blood vessels identified at the surgical site for the registration of the endoscopic imaging data with the additional imaging data includes initially generating the registration of the endoscopic imaging data with the additional imaging data.

8. The system of claim 1, wherein the using of the differentiated set of blood vessels identified at the surgical site for the registration of the endoscopic imaging data with the additional imaging data includes correcting the registration of the endoscopic imaging data with the additional imaging data subsequent to an initial generation of the registration.

9. The system of claim 1, wherein the using of the differentiated set of blood vessels identified at the surgical site for the registration of the endoscopic imaging data with the additional imaging data includes generating or correcting a set of alignment parameters configured to define a spatial transformation between the endoscopic imaging data and the additional imaging data.

10. The system of claim 1, wherein the using of the differentiated set of blood vessels identified at the surgical site for the registration of the endoscopic imaging data with the additional imaging data further includes:
accessing the endoscopic imaging data from an endoscope capturing the endoscopic imaging data;
accessing the subsurface imaging data from an ultrasound module performing the subsurface image scan as an ultrasound scan; and
accessing the alignment parameters representative of the registration of the endoscopic imaging data with the subsurface imaging data.

11. The system of claim 1, wherein:
the using of the differentiated set of blood vessels identified at the surgical site for the registration of the endoscopic imaging data with the additional imaging data further includes accessing auxiliary data representative of an additional feature present at the surgical site and distinct from the differentiated set of blood vessels; and
the generating or correcting of the registration includes:
anchoring an alignment of the endoscopic imaging data and the additional imaging data based on the first and second locations and with respect to a viewpoint, and
refining the alignment of the endoscopic imaging data and the additional imaging data based on the auxiliary data.

12. The system of claim 11, wherein the additional feature that is represented by the auxiliary data and that is present at the surgical site comprises non-vasculature anatomy.

13. The system of claim 11, wherein the additional feature that is represented by the auxiliary data and that is present at the surgical site comprises a cautery mark applied to surface anatomy to mark the surface anatomy in preparation for an operation.

14. The system of claim 1, wherein:
the using of the differentiated set of blood vessels identified at the surgical site for the registration of the endoscopic imaging data with the additional imaging data further includes detecting a user selection of the differentiated set of blood vessels; and
the determining of at least one of the first and second locations of the differentiated set of blood vessels is performed based on the detected user selection of the differentiated set of blood vessels.

15. The system of claim 1, wherein:
the subsurface imaging data from the subsurface imaging scan is doppler ultrasound data scanned by an ultrasound module; and the identifying of the differentiated set of blood vessels is based on at least one of blood flow direction, blood vessel diameter, or blood vessel pattern.

16. The system of claim 1, wherein:
the processor is further configured to execute the instructions to validate the subsurface imaging data as an ultrasound module performing the subsurface image scan provides the subsurface imaging data; and
the using of the differentiated set of blood vessels identified at the surgical site for the registration of the endoscopic imaging data with the additional imaging data is performed based on the validating of the subsurface imaging data.

17. The system of claim 1, wherein the differentiated set of blood vessels identified at the surgical site comprises one of:
arteries differentiated from other types of blood vessels at the surgical site; or
veins differentiated from other types of blood vessels at the surgical site.

18. The system of claim 1, wherein the differentiated set of blood vessels identified at the surgical site comprises a geometric pattern of blood vessels differentiated from the other blood vessels at the surgical site.

19. A system comprising:
a memory storing instructions; and
a processor communicatively coupled to the memory and configured to execute the instructions, intraoperatively during a surgical operation at a surgical site, to:
access intraoperative endoscopic imaging data from an endoscope,
access intraoperative subsurface imaging data from a subsurface imaging module,
access alignment parameters representative of a registration of the intraoperative endoscopic imaging data with the intraoperative subsurface imaging data,
access preoperative scan data captured by way of an additional imaging modality distinct from an endoscopic imaging modality, the preoperative scan data representative of a three-dimensional ("3D") model of anatomy at the surgical site,
identify a differentiated set of blood vessels differentiated from other blood vessels at the surgical site based on the intraoperative subsurface imaging data and the alignment parameters, and
use the differentiated set of blood vessels identified at the surgical site for a registration of the intraoperative endoscopic imaging data with the preoperative scan data representative of the 3D model of the anatomy at the surgical site,
wherein the using of the differentiated set of blood vessels identified at the surgical site for the registration of the endoscopic imaging data with the additional imaging data includes:
determining, based on the subsurface imaging data and alignment parameters representative of a registration of the endoscopic imaging data with the subsurface imaging data, a first location, with respect to anatomy as represented by the endoscopic imaging data, of the differentiated set of blood vessels identified at the surgical site;
determining a second location, with respect to the anatomy as represented by the additional imaging data, of the differentiated set of blood vessels; and
generating or correcting, based on the first and second locations, the registration of the endoscopic imaging data with the additional imaging data.

20. A method comprising:
identifying, by an image registration system, a differentiated set of blood vessels differentiated from other blood vessels at a surgical site based on subsurface imaging data from a subsurface image scan at the surgical site; and
using, by the image registration system, the differentiated set of blood vessels identified at the surgical site for a registration of endoscopic imaging data from an endoscopic imaging modality with additional imaging data from an additional imaging modality,
wherein the using of the differentiated set of blood vessels identified at the surgical site for the registration of the endoscopic imaging data with the additional imaging data includes:
determining, based on the subsurface imaging data and alignment parameters representative of a registration of the endoscopic imaging data with the subsurface imaging data, a first location, with respect to anatomy as represented by the endoscopic imaging data, of the differentiated set of blood vessels identified at the surgical site;
determining a second location, with respect to the anatomy as represented by the additional imaging data, of the differentiated set of blood vessels; and
generating or correcting, based on the first and second locations, the registration of the endoscopic imaging data with the additional imaging data.

* * * * *